(12) United States Patent
Reed et al.

(10) Patent No.: US 12,144,894 B2
(45) Date of Patent: Nov. 19, 2024

(54) SHAPE-GUIDED CONTROLLED RELEASE AND RETENTION WITH STRUCTURES INCLUDING CROSSLINKED POLY(GLYCEROL SEBACATE)

(71) Applicant: THE SECANT GROUP, LLC, Telford, PA (US)

(72) Inventors: Stephanie Reed, Conshohocken, PA (US); Alexander M. Stahl, Haverford, PA (US); Manasi Chawathe Baker, Ambler, PA (US); Peter D. Gabriele, Frisco, TX (US); Amanda K. Weber, Macungie, PA (US)

(73) Assignee: THE SECANT GROUP, LLC, Telford, PA (US)

( * ) Notice: Subject to any disclaimer, the term of this patent is extended or adjusted under 35 U.S.C. 154(b) by 203 days.

(21) Appl. No.: 17/365,139

(22) Filed: Jul. 1, 2021

(65) Prior Publication Data

US 2022/0031624 A1    Feb. 3, 2022

Related U.S. Application Data

(60) Provisional application No. 63/057,952, filed on Jul. 29, 2020.

(51) Int. Cl.
*A61K 9/48* (2006.01)
*A61K 45/06* (2006.01)

(52) U.S. Cl.
CPC ............ *A61K 9/4866* (2013.01); *A61K 45/06* (2013.01)

(58) Field of Classification Search
CPC .................................................. A61K 9/0065
See application file for complete search history.

(56) References Cited

U.S. PATENT DOCUMENTS

| | | | |
|---|---|---|---|
| 9,359,472 B2 | 6/2016 | Nicholson et al. | |
| 10,525,140 B2 | 1/2020 | Wroblesky et al. | |
| 10,556,217 B2 | 2/2020 | Lu et al. | |
| 10,568,962 B2 | 2/2020 | Gabriele et al. | |
| 2007/0104754 A1* | 5/2007 | Sterling | A61F 2/04 424/423 |
| 2010/0215732 A1* | 8/2010 | Mintchev | A61K 9/0065 424/94.1 |
| 2011/0082419 A1* | 4/2011 | Mintchev | A61K 9/4866 604/57 |
| 2013/0231412 A1 | 9/2013 | Langer et al. | |
| 2015/0320542 A1* | 11/2015 | Gabriele | A61F 2/88 623/1.13 |
| 2015/0342877 A1* | 12/2015 | Menachem | A61K 9/0065 604/890.1 |
| 2017/0106099 A1* | 4/2017 | Bellinger | A61M 31/002 |
| 2018/0035871 A1 | 2/2018 | Joshi et al. | |
| 2018/0280912 A1* | 10/2018 | Lu | A61L 24/0036 |
| 2018/0311154 A1 | 11/2018 | Kanasty et al. | |
| 2019/0231697 A1 | 8/2019 | Bellinger et al. | |
| 2019/0254966 A1 | 8/2019 | Bellinger et al. | |
| 2019/0262265 A1 | 8/2019 | Bellinger et al. | |
| 2020/0061240 A1 | 2/2020 | Reed et al. | |
| 2020/0146979 A1 | 5/2020 | Kanasty et al. | |
| 2020/0281851 A1 | 9/2020 | Grant et al. | |
| 2021/0196627 A1 | 7/2021 | Grant et al. | |

FOREIGN PATENT DOCUMENTS

| | | |
|---|---|---|
| KR | 20170015389 A | 2/2017 |
| KR | 20170016960 A | 2/2017 |
| WO | 2015191920 A1 | 12/2015 |
| WO | 2015191922 A1 | 12/2015 |
| WO | 2015191925 A1 | 12/2015 |
| WO | 2020041489 A1 | 2/2020 |
| WO | 2020117855 A1 | 6/2020 |
| WO | 2020191229 A1 | 9/2020 |
| WO | 2020191231 A1 | 9/2020 |
| WO | 2021092483 A1 | 5/2021 |
| WO | 2021092484 A1 | 5/2021 |
| WO | 2021092486 A1 | 5/2021 |
| WO | 2021092487 A1 | 5/2021 |
| WO | 2021092491 A1 | 5/2021 |

OTHER PUBLICATIONS

Klausner et al., "Expandable gastroretentive dosage forms", Journal of Controlled Release, vol. 90, pp. 143-162 (2003).

* cited by examiner

*Primary Examiner* — Robert A Wax
*Assistant Examiner* — William Craigo
(74) *Attorney, Agent, or Firm* — McNees Wallace & Nurick LLC

(57) ABSTRACT

A delivery system is described that includes a controlled release device that includes a crosslinked poly(glycerol sebacate) (PGS) or other glycerol ester and a controlled release compound, the controlled release device being provided in a contracted state and being expandable to a three-dimensional expanded state in a target location. The delivery systems provides an expandible, flexible biodegradable elastomer loaded with an active ingredient to allow for extended release for different dosage forms for either human or animal health products in vivo, delivered through the gastrointestinal tract.

25 Claims, 11 Drawing Sheets

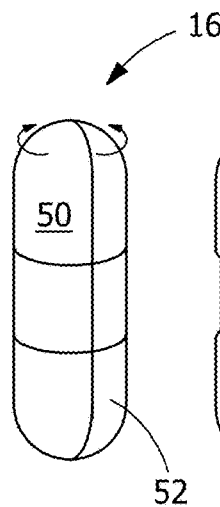
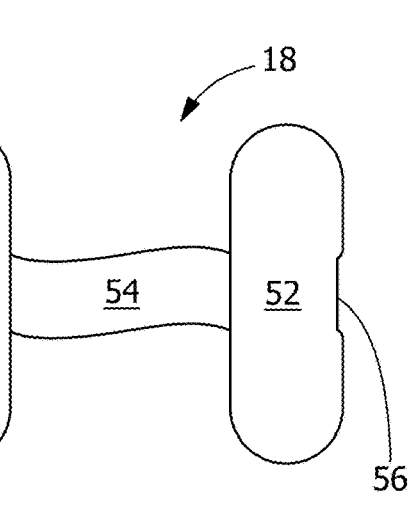
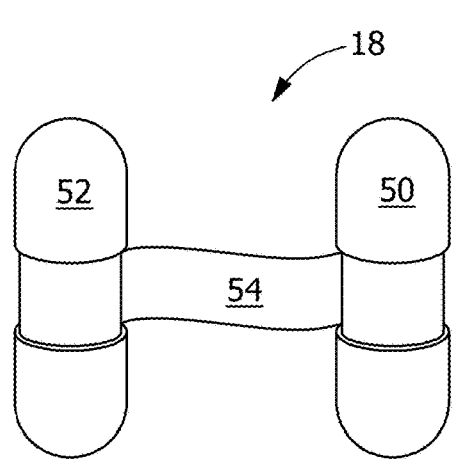
FIG. 8A  FIG. 8B  FIG. 8C
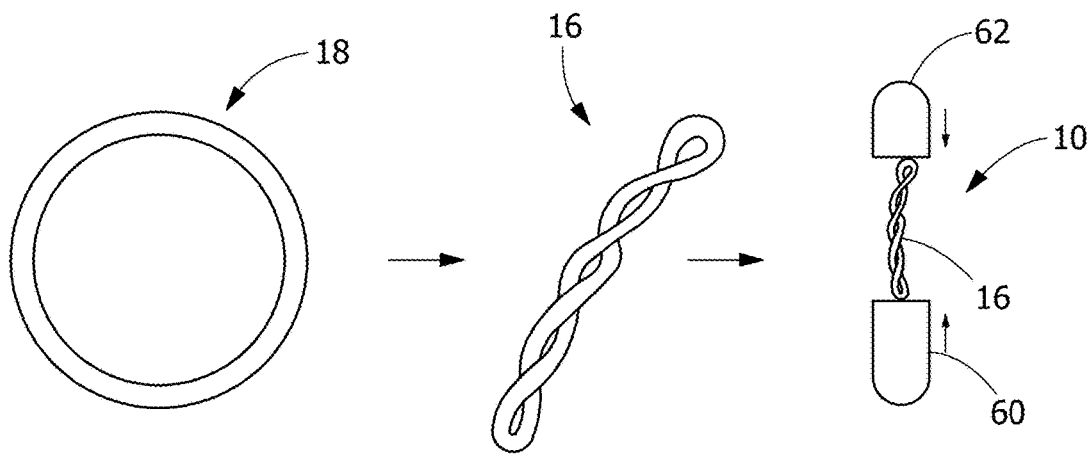
FIG. 9

SHAPE-GUIDED CONTROLLED RELEASE AND RETENTION WITH STRUCTURES INCLUDING CROSSLINKED POLY(GLYCEROL SEBACATE)

RELATED APPLICATIONS

This application claims the benefit of and priority to U.S. Application No. 63/057,952 filed Jul. 29, 2020, which is hereby incorporated by reference in its entirety.

FIELD

The present disclosure is generally directed to controlled release devices. More specifically, the present disclosure is directed to shape-guided controlled release and retention structures including poly(glycerol sebacate) (PGS).

BACKGROUND

Gastroretentive devices are designed to physically remain in the stomach for extended periods of time for extended release of a drug. Eventually, however, there must be a safe mechanism by which the gastroretentive device leaves the stomach and eventually the body of the individual. Typically this occurs by degradation of the gastroretentive device until smaller portions of the device are physically able to pass through the remainder of the gastrointestinal tract.

Biodegradable polymers like poly(lactic-co-glycolic acid) (PLGA) exhibit accelerated degradation under acidic degradation, and this bulk degradation mechanism results in PLGA quickly losing its mechanical integrity during the swelling and polymer chain scission of the bulk degradation. This degradation behavior likely rules out PLGA, polylactic acid (PLA), and poly(glycolic acid) PGA for gastroretentive devices, because the large shape necessary to keep the device from passing through the pyloric sphincter into the small intestine prematurely cannot be maintained well or for very long.

Moreover, commercial biodegradable polymers, such as polycaprolactone (PCL) and PLGA, rely on diffusion for drug delivery and accordingly exhibit first order release. As a result, they face difficulty sustaining release at high loadings greater than 50% w/w. Because gastrointestinal drug delivery is less efficient due to a large amount of active pharmaceutical ingredient (API) ending up in the liver during first pass metabolism, the demand for high drug loading within the polymer device is heightened.

A known multi-component, complex gastroretentive device includes an elastomeric central hub and a number of drug-loaded polymer arms sticking outward from the hub. The arms of the gastroretentive device are connected to the central hub by biodegradable linkers. Once a biodegradable linker breaks down, the drug-loaded polymer arm falls off and becomes free floating, and all pieces are then small enough to pass through the pyloric sphincter into the small intestine and eventually pass through the bowel into stool. The drug-loaded polymer is a stiff thermoplastic, such as PCL. While PCL may provide a multi-week, steady drug release, stiff polymers such as PCL pose issues in the stomach and in the downstream intestine, such as the possibility of blockage or puncture by the polymer arms that are passing through the bowel, as well as the other shortcomings of PCL as already described regarding release at high loadings.

There is a need for a gastroretentive device that provides sustained retention and sustained controlled release of drug and that biodegrades in a manner that permits safe travel through the entire gastrointestinal tract.

SUMMARY

At a high level, aspects of the technology disclosed relate to crosslinked glycerol esters, such as poly(glycerol sebacate) urethane (PGSU) or another crosslinked PGS variant, that provide controlled release from different dosage forms in a drug delivery application, for either human or animal health products in vivo, delivered through the gastrointestinal tract.

In one aspect, a delivery system includes a controlled release device including crosslinked PGS and a controlled release compound. In exemplary embodiments, the PGS is crosslinked, such as by urethane chemistry to form PGSU; by thermosetting; by acrylate chemistry to form poly(glycerol sebacate) acrylate (PGSA); or by photopolymerization chemistry, for example. The controlled release device is provided in a contracted state and expands to a three-dimensional expanded state in a target location.

In another aspect, a process of forming a delivery system includes forming a controlled release device expandable to a three-dimensional expanded state. The controlled release device includes crosslinked PGS and a controlled release compound. The process further includes confining the controlled release device in a delivery vehicle in a contracted state to form the delivery system.

In still another aspect, a method of treatment includes orally administering a delivery system to a patient in need thereof. The delivery system includes a controlled release device including crosslinked PGS and a controlled release compound. The controlled release device is provided in a contracted state and expands to a three-dimensional expanded state in the stomach of the patient. The controlled release device is retained in the stomach by the shape of the three-dimensional expanded state that is initially larger than can pass out of the stomach via the intestinal tract. The delivery system provides direct gastric delivery to the patient.

Delivery systems described herein allow for an entirely flexible device that provides for greater patient comfort and improved patient safety, that allows maintaining a normal digestive function, and that overcomes a void in the art for a controlled release polymer that is simultaneously biodegradable and flexible and which provides for sustained retention and sustained controlled release of a drug while ultimately permitting safe travel through the entire gastrointestinal tract.

Gastroretentive devices should be flexible, biodegradable, and capable of sustaining release, and exemplary embodiments can achieve all three of these features within a single polymer component for the gastroretentive device. Accordingly, in some embodiments, gastroretentive and other controlled release devices can consist of or consist essentially of a crosslinked PGS (such as PGSU) and a drug of interest, without any other polymers needed. This may allow for a simpler manufacturing process as well, such as by casting or molding a single part.

Embodiments of the present disclosure, for example, in comparison to concepts failing to include one or more of the features disclosed herein, provide an elastic controlled release device, provide targeted delivery of a controlled release device, provide retention of a controlled release device, provide sustained controlled release of a controlled release compound, provide safe biodegradation of a gastroretentive controlled release device, provide a customizable delivery system, or combinations thereof.

This summary is intended to introduce a selection of concepts in a simplified form that is further described by this disclosure. The summary is not intended to identify key or essential features of the claimed subject matter nor is it intended to be an aid in determining the scope of the claimed subject matter. Various features and advantages of the present invention will be apparent from the following more detailed description, taken in conjunction with the accompanying drawings which illustrate, by way of example, the principles of the invention.

BRIEF DESCRIPTION OF THE DRAWINGS

FIG. 8A schematically shows a capsule-shaped controlled release device in a contracted state in accordance with an aspect described herein.

FIG. 8B schematically shows a front view of the capsule-shaped controlled release device of FIG. 8A in an expanded state.

FIG. 8C schematically shows a back view of the capsule-shaped controlled release device of FIG. 8A in an expanded state.

FIG. 9 illustrates formation of a controlled release device delivery system in accordance with an aspect described herein.

Where possible, the same reference numbers are attempted to be used throughout the drawings to represent the same parts.

DETAILED DESCRIPTION OF EXEMPLARY EMBODIMENTS

In exemplary embodiments, an expandable, flexible biodegradable elastomer of a crosslinked glycerol ester loaded with an active ingredient provides controlled release from different dosage forms in a drug delivery application, for either human or animal health products in vivo, delivered, for example, through the gastrointestinal tract.

In exemplary embodiments, ultra-long-acting release (e.g. typically intended for drug release lasting at least multiple days and up to multiple months) is provided by a gastroretentive device, which is taken orally and expands to a larger size once inside the stomach. Its size is intended to retain the controlled release device within the stomach for long periods of time, allowing for the release of its drug payload over this time. The controlled release device is intended to eventually biodegrade, either entirely, or into pieces small enough to pass into and through the intestine. It will be appreciated that while exemplary embodiments are particularly well suited for ultra-long-acting release, immediate release (<1 hour) or extended release (<24 hour) dosage forms are also contemplated instead of or in combination therewith.

Figure 1:
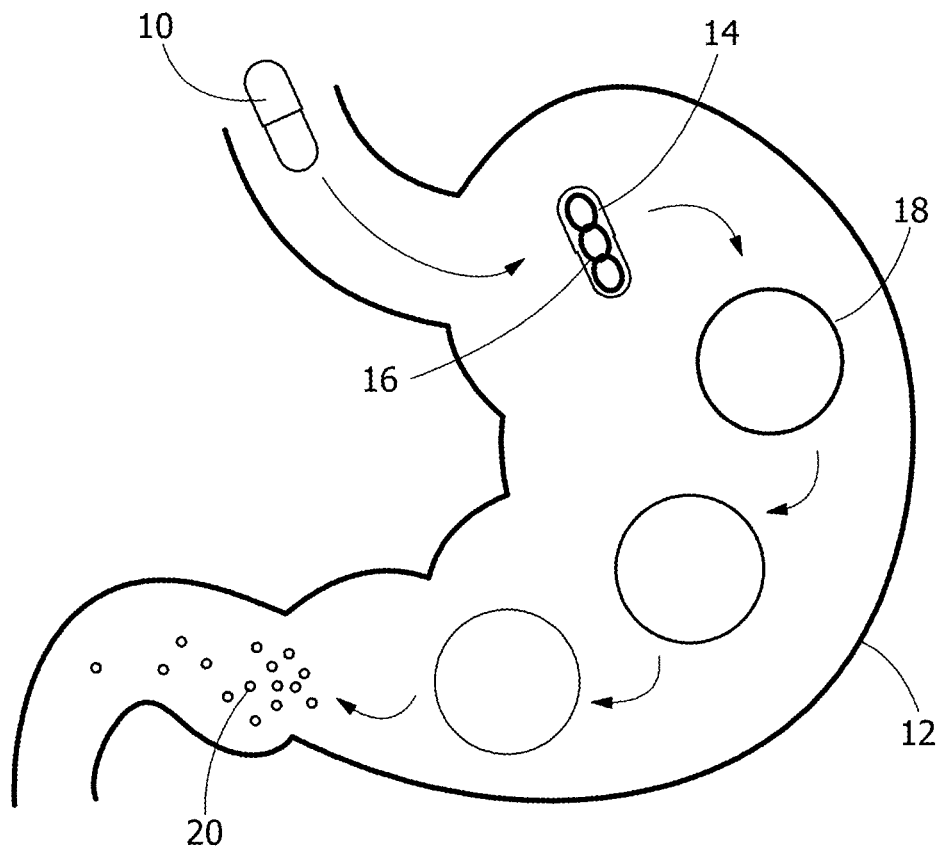
FIG. 1 schematically shows time lapse degradation of a delivery system in a stomach in accordance with an aspect described herein.

Referring generally to FIG. 1, a time-lapse schematic that generally illustrates one aspect is shown with a delivery system 10 initially being ingested into the stomach 12. The delivery system 10 includes a delivery vehicle 14 in the form of a capsule, which contains a contracted controlled release device 16 containing a controlled release compound and which dissolves in a relatively short amount of time, allowing the contracted controlled release device 16 to spring back to its expanded, pre-compacted shape via elastic recovery and that is large enough to be retained within the stomach. The expanded controlled release device 18 includes a crosslinked PGS material and undergoes surface erosion over an extended period of time; the surface erosion results in the expanded controlled-release device 18 maintaining its hydrodynamic radius until the device has eventually eroded significantly enough to break into small particles 20 that pass through the pyloric sphincter into the small intestine.

As used herein, the term "contracted controlled release device" refers to a controlled release device in a contracted state.

As used herein, the term "expanded controlled release device" refers to a controlled release device in an expanded state. In some embodiments, the transition from the contracted state to the expanded state occurs by degradation of a delivery vehicle constraining the shape of the controlled release device. In some embodiments, the transition from the contracted state to the expanded state occurs by swelling of parts of or all of the controlled release device.

As used herein, the term "hydrodynamic radius," as applied to a controlled release device, refers to the radius of the corresponding sphere that best matches the effective space occupied by the device as it dynamically rotates, translates, or experiences changes to its conformation in its expanded state. Because the controlled release device may not be spherical or symmetrical, a 2D projection of the 3D structure varies based on the orientation of the device in relation to the observer. For a given device shape, there may exist a 2D projected footprint having a shortest length compared with all other 2D projections. The controlled release device may be able to pass through a circular opening having a diameter equal to this shortest length. For the purposes of the present disclosure, the hydrodynamic radius of the controlled release device is described as half of the longest length dimension, and correspondingly the expanded state diameter is equal to the longest length dimension.

As used herein, the term "bend radius" refers to the minimum radius that the controlled release device can be bent while maintaining elastic recovery without deforming plastically or incurring damage. Bend radius is measured to the inside curvature of the bend.

In exemplary embodiments, a delivery system includes a controlled release device including a crosslinked glycerol ester polymer such as a poly(glycerol sebacate) (PGS) polymer and a controlled release compound. As used herein, a PGS resin composition may include any oligomer or polymer made from glycerol and sebacic acid. PGS resin compositions may include different stoichiometric ratios of glycerol and sebacic acid, different molecular weights, different degrees of branching, and different polydispersity based on preferred properties of the controlled release device. In exemplary embodiments, the PGS resin composition is formed by a water-mediated synthesis process, such as described in U.S. Pat. No. 9,359,472, issued Jun. 7, 2016, incorporated herein by reference.

The PGS chemistry permits the PGS-based polymer to have a glycerol:sebacic acid ratio that may be selected within a wide range from a high sebacic acid content to a high glycerol content depending on the desired properties for the controlled release device. The PGS resin may include a stoichiometric ratio of glycerol:sebacic acid between 1:0.25 and 1:2, alternatively between 1:0.5 and 1:1.5, alternatively between 1:0.75 and 1:1.25, or any value, range, or sub-range therebetween. For example, tuning of the glycerol:sebacic acid ratio may enhance controlled release compound solubility and/or permeability. Use of a PGS-based polymer may obviate including solubility and/or permeability enhancers frequently included in the formulation of conventional oral dosage forms to improve gastrointestinal bioavailability.

PGS is crosslinkable to form an elastomer and is biocompatible and biodegradable, reduces inflammation, improves healing, and has antimicrobial properties, all of which make it useful for the applications described herein.

In one embodiment the PGS or other glycerol ester polymer is crosslinked, such as a poly(glycerol sebacate) urethane (PGSU) in which the PGS is crosslinked by urethane chemistry to form the PGSU. Crosslinking may also occur by thermosetting, by acrylate chemistry with PGS to form poly(glycerol sebacate) acrylate (PGSA), by photopolymerization chemistry, or combinations thereof.

The controlled release device is provided for delivery in a contracted state and expands to a three-dimensional expanded state in a target location.

In exemplary embodiments, a process of forming a delivery system includes forming the controlled release device expandable to a three-dimensional expanded state. The process further includes confining the controlled release device in a delivery vehicle in a contracted state to form the delivery system.

In exemplary embodiments, a method of treatment includes orally administering delivery systems in accordance with exemplary embodiments to a patient in need thereof. The delivery system includes providing the controlled release device in a contracted state that expands to a three-dimensional expanded state in the stomach of the patient. The controlled release device is retained in the stomach by the shape of the three-dimensional expanded state. The delivery system provides direct gastric feeding to the patient. The patient may be, for example, a dysphagic patient, a premature infant, an unconscious patient, a surgically compromised patient, or a traumatically injured patient.

The delivery system is swallowed through the oral route of administration and the delivery vehicle disintegrates quickly once inside the stomach. Once the delivery vehicle breaks down, the controlled release device quickly pops open and expands to its original shape via a shape recovery effect.

The controlled release device begins degrading through surface erosion, with the acidic environment of the stomach affecting the rate of degradation of the crosslinked PGS. The dimensions and shape of the controlled release device also affect the rate of degradation of the crosslinked PGS. Throughout the erosion, the controlled release compound is released in a controlled manner. Crosslinked PGS polymers undergo surface erosion that provides linear, zero-order release kinetics. The polymer surface area can be an important parameter for controlling surface erosion-driven drug release. Crosslinked PGS surface erosion allows the controlled release device to remain large in size, intact, and with structural integrity, as opposed to polymers that degrade through bulk erosion, such as PLGA, PLA, PGA, PCL, and polyethylene glycol (PEG), all of which become soft and pulp-like during degradation.

In exemplary embodiments, the size of the expanded controlled release device is large enough, both initially and over time, to stay and be retained inside the stomach for a predetermined amount of time of at least one day or more, such as two days, three days, four days, five days, six days, a week, multiple weeks, a month, or up to multiple months, if desired for a particular application and generally, but not necessarily, less than six months. After the predetermined length of time, the controlled release device finally becomes soft and degrades into many small particles, but this loss in mechanical properties is more of a sudden drop off, not a steady decline like with bulk degrading polymers. The combined degradation profile and mechanical strength profile is believed to be at least partially attributable to the surface erosion demonstrated by PGS elastomers, which may be formed both as thermoplastic and thermoset elastomers.

The elastomeric flexibility of crosslinked PGS also makes it better for patient comfort while in the stomach during body movement, food ingestion, food digestion, and food movement through to the intestine. Patient safety is also improved, as the crosslinked PGS reduces the risk of blockage or of irritating or puncturing the stomach lining that can occur with conventional gastroretentive devices made with rigid polymers. After the crosslinked PGS has degraded to the point where the controlled release device can leave the stomach, the flexibility of particles and pieces is also more comfortable and safer for the patient, for these same reasons, as it is passing through the gastrointestinal tract.

In exemplary embodiments, the delivery system includes a controlled release device that includes the crosslinked PGS in combination with a controlled release compound such as an active ingredient, a nutrient, a pharmaceutical, or a therapeutic ingredient. The controlled release compound is loaded in the crosslinked PGS. The controlled released compound may be loaded either by mixing with the polymer prior to or during forming the device or by chemically attaching to the crosslinked PGS.

In some embodiments, a controlled release device consists essentially of crosslinked PGS loaded with one or more controlled release compounds. That is, in some embodiments, the controlled release device excludes any secondary polymer components that are non-PGS-based. In some embodiments, the controlled release device includes a uniform crosslinking density of crosslinked PGS throughout. When the polymeric portion of the controlled release device is entirely elastomeric PGSU, the entire controlled release device is flexible and can be manipulated through twisting, folding, bending, and/or coiling to fit into an oral delivery vehicle.

In exemplary embodiments, the controlled release device is formed by injection molding the crosslinked PGS and controlled release compound to the shape of the expanded state. The controlled release device elastically returns to the expanded state after release from the delivery vehicle.

As previously discussed, in some embodiments the crosslinked PGS is preferably PGSU. PGSU is formed by crosslinking a PGS resin and an isocyanate. Appropriate isocyanates may be aliphatic or aromatic in structure and may include, but are not limited to, hexamethylene diisocyanate (HDI), methylene diphenyl diisocyanate (MDI), toluene diisocyanate (TDI), isophorone diisocyanate (IPDI), methylenebis(cyclohexyl isocyanate) (HMDI), tetramethylxylene diisocyanate (TMXDI), aliphatic isocyanates, aromatic isocyanates, aliphatic-aromatic combination isocyanates, and/or blocked isocyanates.

A controlled release device of PGSU loaded with a controlled release compound can achieve steady controlled release for a time period of multiple weeks to even more than a year, depending on the crosslinking density of the PGSU. Since PGSU is surface eroding, it is capable of maintaining its mechanical form without losing mechanical integrity for longer periods of time than a bulk eroding polymer. PGSU also maintains excellent flexibility, as well as controlled release at up to 80% w/w loading of controlled release compound, and is able to bend in half and spring back with full elasticity and no measurable plastic deformation. This elastic resilience, surface erosion, and high drug loading, coupled with the steady release of loaded controlled release compound over long durations, makes PGSU a preferred material for the delivery systems described herein. Even if a portion of the controlled release device degrades into smaller pieces that pass into the intestine, the pieces are more flexible, more comfortable, and safer for the patient to pass through the digestive tract and the bowel than the pieces of conventional gastroretentive devices.

According to an aspect, controlled release devices having a polymer component with flexural modulus of between 1-30 MPa, alternatively 1-12 MPa, and in some cases less than 10 MPa (as used herein, flexural modulus is quantified by three-point bending). Additionally, controlled release devices comprising a drug-loaded polymer may exhibit a higher stiffness than the polymer component alone and have a flexural modulus between 1-100 MPa, alternatively 1-50 MPa, and in some cases less than 10 MPa. Flexural modulus is primarily related to the composition and may be significantly impacted by the drug loading and drug particle properties, such as particle size and morphology, within the formulation. In contrast, bend radius is dependent on both composition and geometric dimensions of the part. In one aspect, controlled release devices having a bend radius of less than 5 millimeters (mm), alternatively less than 4 mm, and in some cases less than 3 mm may be suitable.

In exemplary embodiments, the entire controlled release device is composed of a single component of PGSU loaded with controlled release compound, without the need for a hub or biodegradable linkers. In exemplary embodiments, the PGSU is manufactured by injection molding into a desired shape, component, or device from a PGS resin starting material. In exemplary embodiments, the controlled release device provides in vivo controlled release following oral delivery.

The PGSU may be formulated with a stoichiometric ratio of isocyanate-to-hydroxyl between 1:0.25 and 1:4, 1:0.25 and 1:2, alternatively between 1:0.25 and 1:1.5, alternatively between 1:0.25 and 1:1.25, or any value, range, or sub-range therebetween. In particular, the range between 1:1 and 1:4, alternatively between 1:1 and 1:2, or alternatively between 1:1 and 1:1.25, may be especially suitable for imparting flexibility to the devices, particularly for providing suitable flexibility even at high drug loadings. The PGSU may be formed from PGS resin selected for its molecular weight, polydispersity index, reaction process, degree of branching, acid number, hydroxyl number, and glycerol-to-sebacic acid stoichiometric ratio, such as described in U.S. Patent Application Publication No. 2020/0061240, published Feb. 27, 2020, incorporated herein by reference.

PGS resin starting material for creating a crosslinked PGS material may have a highly-branched architecture or may be more linear. The PGS resin may be functionalized with chemical moieties, such as for crosslinking or conjugation of therapeutic agents. The PGS resin may contain catalysts, such as to aid crosslinking or accelerate reaction time. The PGS resin may contain processing aids, plasticizers, solvents, excipients, PGS oligomers, free glycerol, or free sebacic acid to improve flexibility. In some embodiments, PGS resin starting material is highly-branched, has a polydispersity index in the range of 7-12, has a molecular weight in the range of 13,000-19,000 Da, has a glycerol-to-sebacic acid stoichiometric ratio of 1:1, has a hydroxyl value in the range of 160-240, or combinations thereof.

In some embodiments, the PGS elastomer composition includes different crosslinking densities, which in turn may augment the biodegradation time, mechanical stiffness, pH-dependent degradability, and API release kinetics.

In some exemplary embodiments, the controlled release device may be manufactured by injection molding with PGS resin starting material in either a solvated or a solvent-free state. Solvents may include but are not limited to, acetone, propyl acetate, ethyl acetate, tetrahydrofuran, acetonitrile, dimethyl sulfoxide, dimethyl formamide, chloroform, dichloromethane, carbon tetrachloride, methanol, ethanol, butanol, or a combination of one or more of these solvents. PGS solutions ranging from 30% to 90% or 40% to 80% w/w, in the solvents listed above, may be suitable for manufacturing PGSU delivery devices with suitable flexibility. Preferred PGS solutions range between 40% to 60% w/w in 1:1 w:w acetone:propyl acetate ratio. Solvents can be evaporated after PGSU curing in a post-processing treatment, for example, evaporation at 40° C. and 10 torr for six days. The rate of evaporation and surface area exposed to evaporation may also impact flexibility. For example, a controlled, slow evaporation rate across a limited air interface may provide a more flexible PGSU while an uncontrolled, fast evaporation rate across a large air interface may provide a more brittle PGSU.

PGSU exhibits minimal swelling (such as, for example, about 1-3% w/w and in some cases less than 1% w/w), which is advantageous in many embodiments over more hydrophilic polymers like PLGA that exhibit greater swelling as a mechanism that contributes to the degradation process and in turn makes that class of polymers less suitable for ultra-long release applications.

PGSU is also fluid impermeable, which protects the active drug payload in the center of the cross-section of the device from the harsh acidic environment of the stomach. This can be especially useful for sensitive or unstable API payloads, such as peptides, proteins, or other biologics.

Crosslinked PGS compositions such as PGSU are also more survivable in the acidic environment of the stomach compared to PLGA, which exhibits a significant auto-catalyzed degradation in acidic conditions. PGSU is more robust to acidic or basic pH than these conventional biodegradable polyesters like PLGA and PCL, meaning PGSU degradation in acidic or basic pH is slower and more controlled. As such, PGSU maintains mechanical integrity and shape-designed hydrodynamic radius during acidic or basic degradation because PGSU degrades through surface erosion, unlike other biodegradable polyesters PLGA and PCL.

Controlled release devices in accordance with exemplary embodiments can be shelf stable at room temperature and room humidity for at least one year, and PGSU has advantages over other polyesters such as PLGA in this regard. PGSU hygroscopicity is also an improvement over other polyesters, similar to its minimal swellability.

Notably, PGSU crosslinking formulations that are shelf stable at room temperature and room humidity are very slow degrading when implanted parenterally, especially in thick shapes. For example, cylindrical rods without any drug loading, having a diameter of 2-3 mm and at a crosslinking that creates very flexible rods, were observed to display only around 3% mass loss at 3 months in both in vitro and in vivo in rat subcutaneous models. More highly crosslinked, stiffer cylindrical rods, again without any drug loading and having a diameter of 2-3 mm, displayed similarly minimal mass loss at 8 months in vivo in a rat subcutaneous model. While this can be advantageous in some applications, these degradation times may be slower than desired for some gastroretentive applications. It may be desirable for gastroretentive devices to remain in the stomach for at least 1 week up to about 12 months, alternatively up to about 6 months, alternatively up to about 3 months, alternatively up to about 1 month, or any range or subrange in between. There may be, for example, reasons based on human factors and use case assessment to not want a gastroretentive device to remain in the stomach for greater than 6 months. Accordingly it may be desirable for a PGSU formulation to degrade completely within the stomach within 6 months.

One method of accelerating PGSU degradation is to use a lower crosslinked PGSU formulation. Lower crosslinking ranges (e.g. stoichiometric ratio of isocyanate-to-hydroxyl less than 1:2, such as, for example, 1:3, 1:4, 1:8, 1:10, or lower) may not be shelf stable at room temperature and room humidity and the implantable product may suffer from clouding and stiffening when stored at ambient conditions. Accordingly, it may not be practical to simply lower PGSU crosslinking density until a faster degradation rate is reached. PGS thermoset, PGSU, and other PGS-based crosslinking chemistries degrade more quickly, however, at low and high pH conditions compared to neutral pH. It was demonstrated that PGSU formulations with shelf-stable crosslinking can also degrade more quickly in acidic conditions similar to the stomach, as well as basic conditions similar to the intestine. Leveraging this pH-sensitivity provides a solution for the otherwise potentially undesirably slow degradation observed with shelf-stable crosslinked PGSU.

Another method of accelerating PGSU degradation is to increase the surface area of PGSU, which will speed up surface erosion. This may be achieved by designing and controlling the shape, dimensions, and/or porosity of the controlled release device at the start of deployment and throughout residence in the stomach during use. Porogens of different morphologies and at different loadings, and corresponding different degrees of interconnectivity, may be included as a method to achieve porosity in PGSU. Water can be spiked into PGS during formulation and/or molding to achieve a porous PGSU foam, since water reacts with isocyanate to create carbon dioxide in the form of bubbles. Alternatively, gasses can be entrained or introduced into PGS during formulation and/or molding to achieve a PGSU foam. Alternatively, blowing agents or pneumatogens can be incorporated into PGS during formulation and/or molding to achieve a PGSU foam or sponge with open-cell or closed-cell architecture. Open-cell foams may expand upon encountering liquid, while closed-cell foams may resist compression. PGSU can be cast into complex shapes with open-cell architectures, multi-faceted features, and/or thin walls, to achieve an increased surface area. Drug release can still be sustained by selecting API particle size and morphology relative to the PGSU wall thickness, such as, for example an API with a particle size of 1-10 micrometer (μm) loaded into PGSU with a 100-μm wall thickness. Alternatively, faster degrading crosslinking units, such as ester linkages, ionic complexes, or others, could be included in addition to or in place of more slowly degrading crosslinking moieties, such as urethane linkages.

In exemplary embodiments, the controlled release device is loaded with a controlled release compound, which may be encapsulated by physical mixing within PGS. Alternatively, PGS resin compositions may have different functional moieties, including the controlled release compound, which can be included in the formulation or conjugated to the PGS by covalent attachment to the polymer backbone or an end group during polymer production.

Appropriate controlled release compounds may include, but are not limited to, nutritional doping/bioactive agents, APIs, biologic agents, therapeutic agents, drugs, vaccines, gene and cell transfer technology agents, small sugars, carbohydrates, cholesterols, lipids, vitamins, minerals, metals, nutrient supplements, nutraceutical agents, contrast agents, diagnostic agents, radioactive agents, prophylactic agents, pain management agents, addiction management agents, plant or herbal extracts, or combinations thereof. Appropriate APIs may include, but are not limited to, antibiotics, anti-virals, anti-oxidants, anti-inflammatories, nonsteroidal anti-inflammatory drug (NSAIDs), opioids, anti-depressants, anti-psychotics, insulin, hormones, cannabidiol (CBD), tetrahydrocannabinol (THC), small molecules, large molecules, peptides, proteins, enzymes, growth factors, nucleic acids, small interfering ribonucleic acid (siRNA), RNA interference (RNAi), microRNA, messenger RNA (mRNA), plasmids, viral vectors, vaccine components, deactivated virus materials, antigens, immunological components, adjuvants, breeding adjuvants, or antigens.

The amount of controlled release compound used in the crosslinked PGS material may vary depending on a variety of factors. Loading may be up to a total of about 80% w/w of active drug or other controlled release compound relative to the total implant weight. In one aspect, drug loading of crosslinked PGS is in a range of 5% to 80% w/w. In one aspect, drug loading in the range of 20% to 70% w/w loading, alternatively 30% to 60% w/w loading may be preferred for some PGSU applications. The drug loading is achieved in amounts to yield sustained drug release performance and flexible mechanical properties suitable for gastroretention. Other crosslinked PGS chemistries may exhibit different preferred range of drug loading, with a 5% to 80% w/w drug loading range still expected to be achievable.

The physical properties of the controlled release compound may affect the release rate and flexibility of the device. The controlled release compounds may have particle sizes in the range of 1-100 μm, alternatively 1-50 μm, alternatively less than 10 μm, and in one aspect are in the range of 2 to 5 μm. The controlled release compound may be in crystalline, semi-crystalline, or amorphous form. It will be appreciated that controlled release compound morphology may also affect the release rate and flexibility of the device, and that needle-like drug particles may form an interconnected network different from granule-like drug particles, which may impact the release rate of highly soluble drugs. Alternatively, a controlled release compound loaded in its amorphous form in the device may accelerate release of a poorly water-soluble drug. Controlled release compound morphology may also impact flexibility, since the drug acts as a filler within the polymer that alters stress distribution and crack propagation.

The formulated composition of the crosslinked PGS and controlled release compound is formed into a controlled release device having an expanded three-dimensional shape but that is able to form a collapsed state for ingestion. Generally, a collapsed state capable of fitting into a capsule with a cross-sectional diameter of 9.5 mm and an expanded state having a minimum hydrodynamic radius of 15 mm (diameter of 30 mm) or greater is suitable for gastroretentive applications. Smaller dimensions may be suitable for children, where the pyloric sphincter physiology may be smaller. Different dimensions may be suitable for animals of different species, where the gastrointestinal physiology may differ greatly.

In some exemplary embodiments, a controlled release device is made by casting and forming, preferably by injection molding, into a predetermined shape via tubing or other molding that is pre-formed into the desired expanded shape. In some embodiments, the injection molding is reactive injection molding. In other embodiments, the controlled release device may be cut or stamped from a cast sheet material of the crosslinked PGS elastomer containing the controlled release compound. Additionally or alternatively, additive manufacturing or subtractive manufacturing methods may also provide engineering shaped-charged design advantages to the controlled release device.

In some exemplary embodiments, the flow of material into the mold during device forming imparts a benefit on device flexibility. More specifically, as the formulated blend of drug and PGS resin is flowed into the mold (typically alongside isocyanate and catalyst, when forming PGSU), the polymer chains may orient with the moving front of fluid flow. Similarly, the drug particles may orient with the moving front of fluid flow. The alignment of polymer chains and/or drug particles can provide greater flexibility of the final device. This has been observed when comparing PGSU rings formed by multiple circular passes of extruded infills into a ring-shaped mold versus PGSU rods formed by a single extrusion into a tube-shaped mold. The two shapes and two fabrication methods are otherwise composed of the same drug-loaded formulation and same cross-sectional dimensions, yet the rods demonstrate greater flexibility.

The as-formed elastomeric material forms a flexible controlled release device that has a geometric design and material properties that result in it being compressible to provide delivery through a small orifice but also being expandable, exhibiting shape recovery. As a result, the device springs back to the initial as-formed conformation after being collapsed and contained in a delivery vehicle for delivery into a body cavity and then subsequently liberated from the delivery vehicle once resident in the cavity, such as the stomach. There it returns to and maintains its initial voluminous shape for a pre-determined extended period of time to provide the controlled release of the controlled release compound. In exemplary embodiments, the spring-back behavior of the flexible controlled release device is stable and recoverable after storage on the shelf for at least one year.

While described primarily with respect to oral delivery for use as a gastroretentive device, it will be appreciated that exemplary embodiments may be used in combination with alternative routes of administration which may include, but are not limited to, parenteral delivery, intravaginal delivery, ocular delivery, or any other delivery to a hollow lumen structure, including, but not limited to, urogenital, rectal, aural, or nasopharyngeal.

Figure 2A:
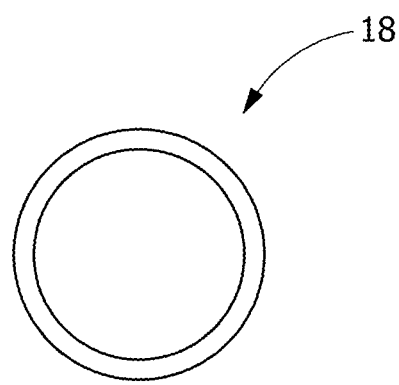
FIG. 2A illustrates a ring-shaped controlled release device in accordance with an aspect described herein.
Figure 2B:
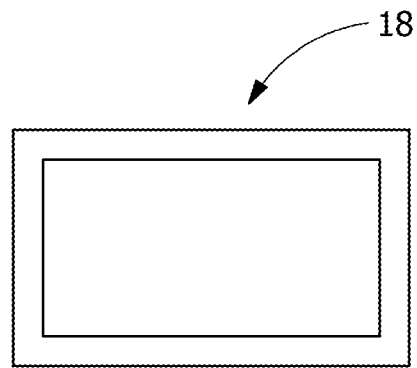
FIG. 2B illustrates a ring-shaped controlled release device in accordance with another aspect described herein.
Figure 2C:
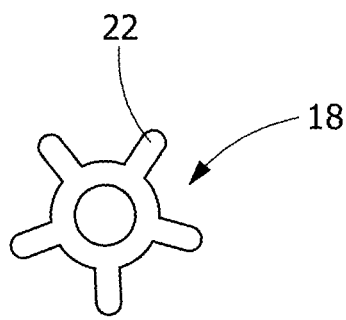
FIG. 2C illustrates a ring-shaped controlled release device in accordance with another aspect described herein.
Figure 2D:
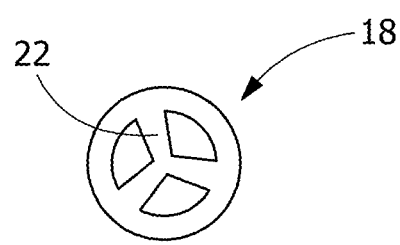
FIG. 2D illustrates a ring-shaped controlled release device in accordance with another aspect described herein.

In some embodiments, the expanded controlled release device 18 has the shape of a ring, as illustrated in FIG. 2A and FIG. 2B, which illustrate circular and rectangular rings, respectively. The ring of the expanded controlled release device 18 may have arms 22 that extend outwardly or inwardly from the ring similar to a ship's wheel or a steering wheel, as illustrated in FIGS. 2C and 2D, respectively.

Figure 3A:
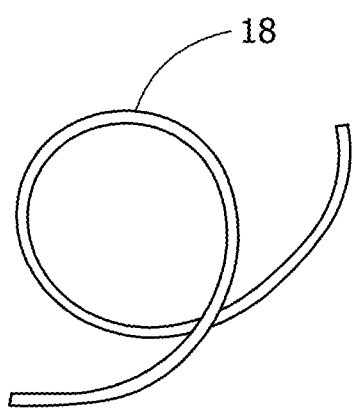
FIG. 3A illustrates a non-ring shaped controlled release device in accordance with an aspect described herein.
Figure 3B:
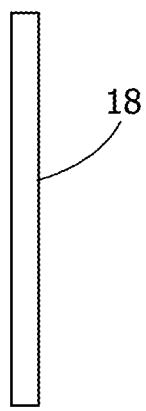
FIG. 3B illustrates a non-ring shaped controlled release device in accordance with another aspect described herein.

In other embodiments, the expanded controlled release device 18 has an elongate structure, such as a coil as illustrated in FIG. 3A, a rod as illustrated in FIG. 3B, or a spiral. In embodiments in which the controlled release device is an elongate structure, it is preferred to provide a curved or coiled geometry, as straight structures may end up in a position to leave the stomach or other cavity prior to the intended residence time.

Other appropriate shapes for the controlled release device in the expanded state may include, but are not limited to, a multi-limb or multi-lobal device such as a star or asterisk, or any other shape with a large hydrodynamic radius to help ensure retention within the cavity in which it is deployed. The controlled release device may be symmetrical or asymmetrical in shape.

Figure 2E:
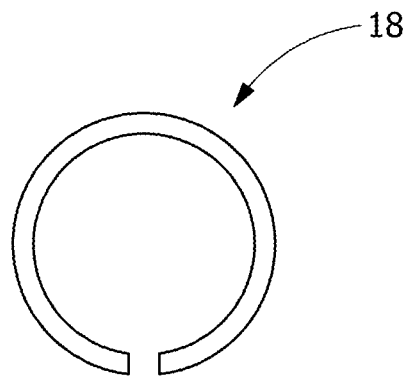
FIG. 2E illustrates a ring-shaped controlled release device in accordance with another aspect described herein.

In some currently preferred embodiments, the expanded controlled release device 18 has the shape of a ring. The ring may be a closed, continuous loop as illustrated in FIG. 2A through FIG. 2D, or the ring may contain a single complete break at a point along its perimeter, as illustrated in FIG. 2E. The break may be a cut, such that the two sides still make physical contact with another or could include a break that includes a missing section along the perimeter that is up to about one half of the total perimeter length, typically a third or less of the total perimeter length, such as about twenty percent or less and in some cases ten percent or five percent or less of the total perimeter length. In some embodiments, a ring containing a single complete break may aid in foldability for compression of the controlled release device within the delivery vehicle as described subsequently in more detail. The break in a ring conformation may aid in the ring springing back to its expanded shape more easily once inside the target cavity and freed from the delivery vehicle.

Figure 4A:
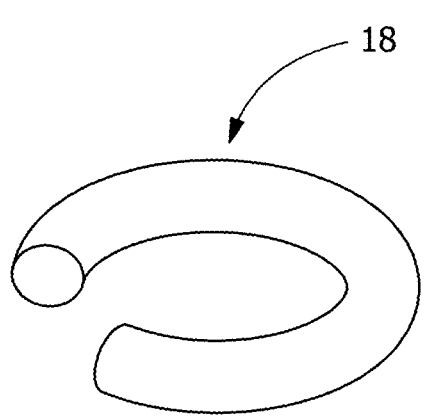
FIG. 4A illustrates a cross-sectional shape for controlled release devices in accordance with an aspect described herein.
Figure 4B:
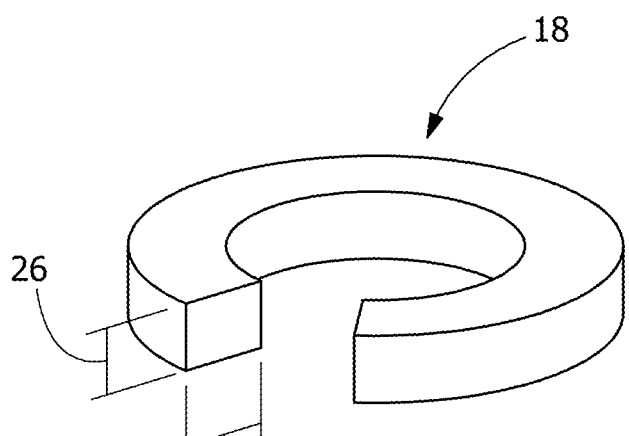
FIG. 4B illustrates a cross-sectional shape for controlled release devices in accordance with another aspect described herein.

The expanded controlled release device 18 may have the shape of a ring having a toroidal shape with a circular cross-section as illustrated in FIG. 4A. In other embodiments, the cross-sectional shape is non-circular, such as the rectangular cross-section shown in FIG. 4B. Expanded controlled release devices 18 having a rectangular cross-sectional shape, particularly those with a high aspect ratio, have the additional advantage of providing a linear release of the controlled release compound during deployment as the polymer erodes, because the surface area is proportional to the thickness of the ring wall in a linear relationship, unlike a circular cross-section that dimensions more significantly as it erodes, because the surface area is proportional to the radius of the ring wall in a second power relationship. The aspect ratio of the rectangular cross-section may vary; in some embodiments, the cross-section may be square. In other embodiments, the width 26 of the cross-section may be several times greater than the thickness 28, similar to a wide rubber band, to provide a high aspect ratio.

Figure 5A:
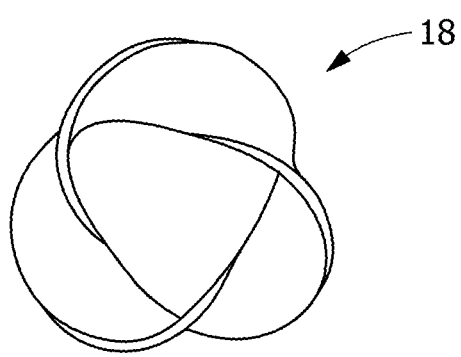
FIG. 5A illustrates a complex-shaped controlled release device in accordance with an aspect described herein.

In some embodiments, expanded controlled release devices 18 in the form of rings have a cross-sectional diameter of 0.5 to 4.5 mm, such as 2 mm to 4 mm in diameter for circular cross-sections. In some embodiments, rectangular cross sections are about 0.75 mm to 2 mm in the thickness direction and about 3 mm to about 6 mm in the width direction although larger and smaller cross-sectional dimensions are contemplated. Rectangular cross-sections with wider cross-sections can also further aid in flexibility and achieving a tighter bend radius. Specific dimensions for a particular application may be adjusted to address bending, stress distribution, and crack propagation. For example, circular cross-sections may be more pliable than other cross-sectional shapes, as evidenced in theoretical relationships for moment of inertia and shear stress during bending. FIG. 5A illustrates an expanded controlled release device 18 in the form of a ring having a rectangular cross section with a width greater than the thickness and further illustrates that embodiments may be manufactured with one or more twists as part of the expanded geometric conformation independent of any twists or folds imparted during manipulation associated with insertion into a capsule during delivery system production.

Figure 5B:
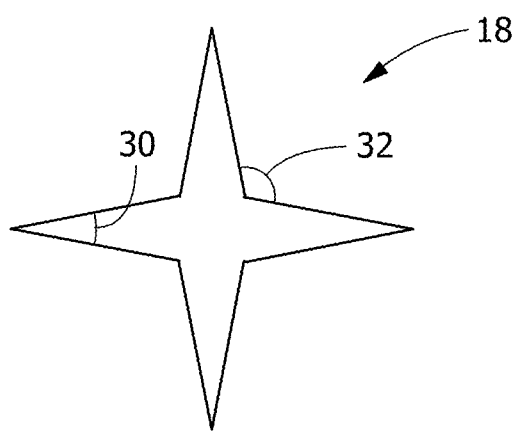
FIG. 5B illustrates a complex-shaped controlled release device in accordance with another aspect described herein.

In some embodiments, the controlled release device design may include corners, points, or flattened regions, twists, or porous regions for enhanced bending and folding. FIG. 5B illustrates an expanded controlled release device 18 in the form of a ring more specifically in the form of a star. While shown with four points, it will be appreciated that the star may include any number of points, such as, for example, five, six, or more points, any of which can be folded at one or more of the inner corners and our outer points to assume the collapsed state with reduced angle strain at the bending points compared to bending a rod or longer segment a full one hundred eighty degrees. An internal angle 30 of the points may range from about 10 to 45 degrees, such as about 25 degrees and may be the same or different for each point, while the external angle 32 between arms may depend on the number of arms but may range, for example, between about 75 degrees to about 145 degrees and which may also be the same or different between arms of the controlled released. For example, a four point star may have an external angle 32 of about 115 degrees, a five point star may have an external angle 32 of about 92 degrees, while a six point star may have an external angle 32 of about 80 degrees.

Figure 5C:
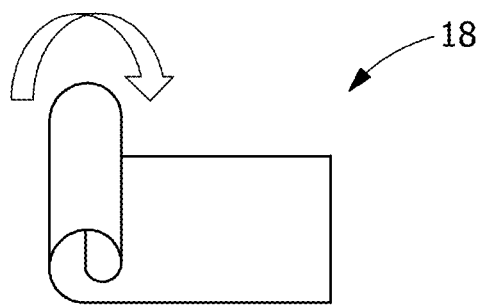
FIG. 5C illustrates a complex-shaped controlled release device in accordance with another aspect described herein.
Figure 5D:
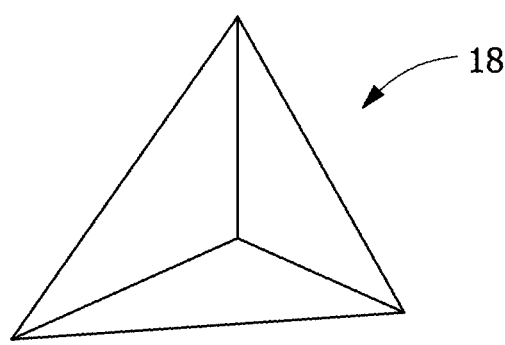
FIG. 5D illustrates a complex-shaped controlled release device in accordance with another aspect described herein.

Because exemplary embodiments can be injection molded, a wide variety of shapes can be formed. Thus, while shown and described primarily with respect to generally flat controlled release devices having open centers, it will be appreciated that conformations having a continuous solid surface may also be employed, provided the device can still be compacted to fit into the delivery vehicle and subsequently return to its expanded conformation via elastic recovery once at the target location. FIG. 5C illustrates an expanded controlled release device 18 in the form a flat sheet that can be rolled up into a tube, while FIG. 5D illustrates a tetrahedron having a reduced angle strain at the bending points compared with bending a straight rod a full 180 degrees. Alternatively, other shapes with angles such as rectangles, parallelograms, polygons, tetrahedra, stars, zigzags, cross-hatches, or accordions may all be used, as well as larger complexity designs that include one or more of the previously mentioned shapes as subregions.

The bend radius may also be tuned for a particular application by changing the cross-sectional thickness of the controlled release device, in addition to changing the cross-sectional shape and the shape in the expanded state. For certain formulations and shapes, the ratio of the device cross-sectional thickness in the expanded state to the narrowest overall dimension in the collapsed state should fall within the range of 1:5 to 1:9, or alternatively 1:2 to 1:5, or alternatively 1:7.5 to 1:20, or alternatively 1:1 to 1:95, in order to achieve optimal capacity to collapse and fit within a capsule or other containment system. For example, in a device capable of collapsing to fit inside a 9.5 mm diameter size 000 capsule, the device cross-sectional thickness in the expanded state may be 1.0 to 1.9 mm, or alternatively 1.9 to 4.75 mm, or alternatively 0.5 to 1.3 mm, or alternatively 0.1 to 9.5 mm. In an embodiment where PGSU is a foam, having either an open-cell or a closed-cell architecture, the device dimensions may be larger than the capsule dimensions, but the PGSU structure is able to be elastically compressed down to fit inside.

Figure 6:
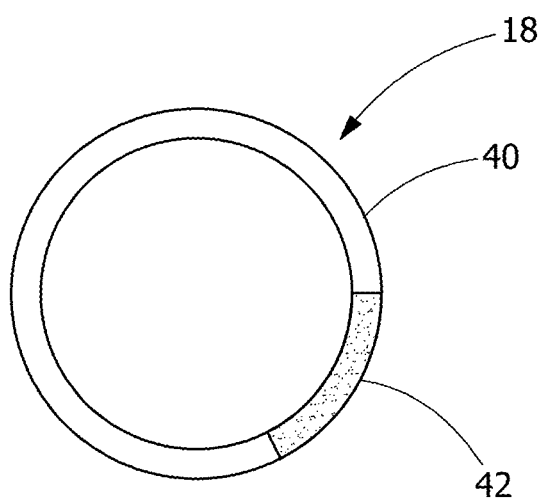
FIG. 6 illustrates a controlled release device in accordance with an aspect described herein.

In some embodiments, the controlled release device includes different sections containing different controlled release compounds and/or crosslinked PGS at different crosslinking densities, as illustrated in FIG. 6, with the ring of the expanded controlled release device 18 having a first section 40 and a second section 42. In such embodiments, the controlled release device provides dual delivery, such as, for example, of a contraceptive agent and an anti-HIV prophylactic or other combination of active ingredients, which may have different solubilities and require different release kinetics, and thus benefit from different polymer matrices for delivery at different rates. The two different controlled release compounds may be at the same or different loadings.

These different sections 40, 42 may be manufactured in a single process during injection molding, such as, for example, by switching the feed stream from a first controlled release compound formulation to a second controlled release compound formulation while filling the mold. This design freedom is not available using thermoplastic manufacturing techniques like hot melt extrusion, since the controlled release compound is loaded into the barrel upstream of mixing and filament extrusion, and there is no ability to switch between different controlled release compounds mid-extrusion.

In some embodiments, the sections 40, 42 are the same PGSU polymer, but at different crosslinking densities. These sections may be manufactured in a single process during injection molding, such as, for example, by varying the mix ratio of the polyol and isocyanate components during reaction injection molding.

In some embodiments, the mix ratio is adjusted mid-process while filling the mold, allowing for zones of differential PGSU crosslinking. Differential PGSU crosslinking allows differential release rates and differential flexibility. PGSU may be crosslinked across a range from highly flexible to somewhat stiff. In some embodiments, the controlled release device thus includes a crosslinking gradient in the crosslinked PGS, thereby providing a degradation gradient that allows one end of the controlled release device to release the controlled release compound first and further provides for better size control.

In some embodiments, the sections 40, 42 are the same PGSU polymer at the same or different crosslinking density, but containing the same controlled release compound at different drug loadings. These sections may be manufactured in a single process during injection molding, such as, for example, by varying the feed stream that supplies the controlled release compound.

Alternatively, two different polymers may be used for the different sections. For example, in some cases, it may be desirable to introduce PGA or other quickly disintegrating polymers for one ring segment or a single arm to break off to deliver medication to the intestine more quickly, while the larger remainder of the device stays resident in the stomach. In these embodiments, the formulations for the different sections could further be adjusted for one section to degrade based on the acidic pH of stomach, while the other degrades based on the basic pH of intestines.

Thus, in some embodiments, a delivery system includes PGSU, any PGS-based polymer, or any pH-sensitive polymer as a component to achieve spatiotemporal release along the gastrointestinal tract, including as a coating or filler particle. This may provide a faster release, such as 24-48 hours, as the delivery vehicle moves through the gastrointestinal tract of a human or animal in an oral drug delivery.

In some embodiments, the reaction injection molding permits an overmolding that provides more complex geometries and devices including parts made from more than one controlled release compound-polymer formulation.

Figure 7:
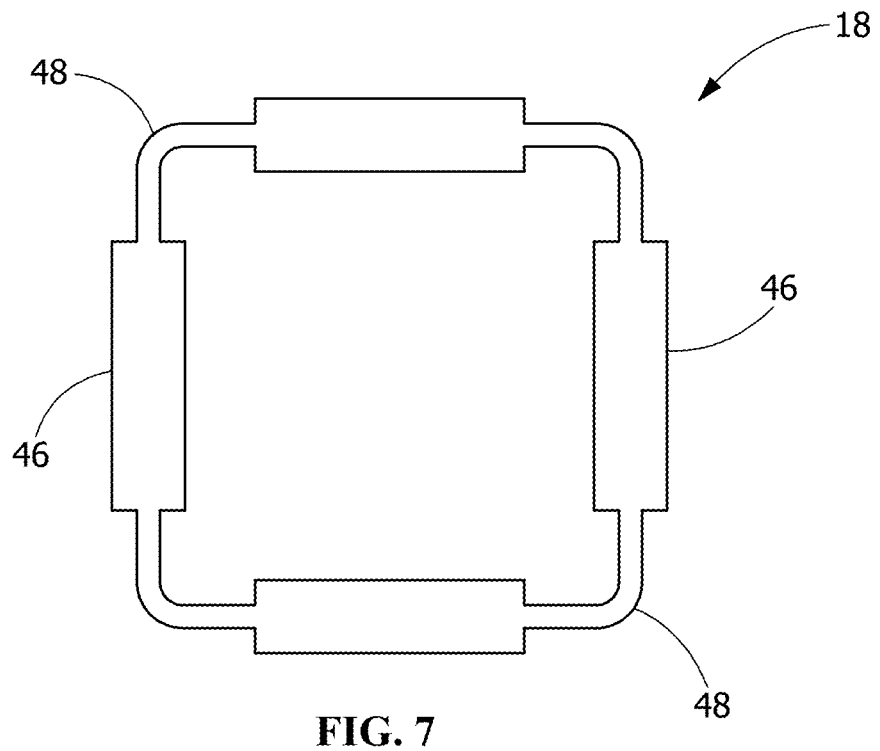
FIG. 7 illustrates a controlled release device in accordance with another aspect described herein.

It will further be appreciated that the dimensions of the controlled release device can be varied in addition to the composition. As illustrated in FIG. 7, the expanded controlled release device 18 includes a rectangular ring with sides 46 that are thick and corners 48 that are thin, which can aid in the bending or compression while still achieving the total drug loading with thicker segments for increased drug payload and thinner segments for increased foldability. In such cases, it may be desirable for the thinner corners 48 to be of a higher crosslinking density than the walls to balance the overall degradation profile. Thinner segments may in addition or alternatively provide shorter degradation or gastric residence times. It is preferred that all segments contain drug loading, though the drug loading level can vary in different segments. The thinner segments to help foldability may be of the same or different cross-sectional shape as the thicker sections. For example, the foldable sections of the corners 48 may be 0.8 to 1.2 mm in thickness and 3 to 4 mm in width in rectangular cross-section, while the payload maximizing sections of the sides 46 may be 4 mm in diameter in circular cross-section, while the entire device is 40% to 60% w/w drug loaded. The foldable segments of the corners 48 are shown shorter in length than the payload maximizing segments of the sides 46. The foldable segments are folded so that the bending moment flexes the thinnest dimension, allowing the tightest bend radius.

In other embodiments, devices with a multi-arm geometry, such as an asterisk, star, or other geometry with multiple pendant arms (e.g., arms 22 as shown in FIG. 2C) attached to a ring or other core can be configured to release individual arms depending on the size and/or specific geometry of the arm or linkage. In such embodiments, one or more arms may be released selectively based on the degradation of the linkage connecting the arm, allowing it to pass through the pyloric sphincter while the core and other arms remain in the stomach. In some embodiments, the arms are loaded with one or more controlled release compounds. In some embodiments, each arm is loaded with the same controlled release compound. In some embodiments, each arm is loaded with a different controlled release compound.

In exemplary embodiments, the degradable linkage is composed of a surface-eroding elastomer, allowing the linkage to provide both the timed release of the arms as well as the flexibility to fold the arms in. In exemplary embodiments, the linkages are molded as a single component that attaches to many arms, where the linkage for a certain arm is a smaller cross-sectional area, leading to complete erosion and release of that arm first. The linkages may include a controlled release compound or be free of a controlled release compound. The linkages may be of the same formulation as the arms or a different formulation.

In yet another aspect, FIG. 8A illustrates a contracted controlled release device 16 of two solid capsule shaped halves 50, 52 sized to fit inside a delivery vehicle 14, the two halves 50, 52 linked by a connector 54 such as an integral rod or sheet segment. As shown in FIG. 8B and FIG. 8C, each half 50, 52 has one flat face and one hemi-cylindrical face and unfurled together like a scroll by unwrapping the connector 54 around the outer surface of one or both half-capsules 50, 52 to form the expanded controlled release device 18. The connector 54 may be wrapped around the outer surface in a manner that adds minimally to the overall dimensions, such as by positioning the furled sheet of the connector 54 in a cutout 56 so the exterior surface of the two halves 50, 52 is flush. Upon deployment, the two half-capsules 50, 52 drift apart in the gastric fluid via elastic recovery to their initial separated conformation, but remain tethered together by the unfurled sheet of the connector 54. This embodiment can fully fill the interior cavity of the delivery vehicle 14, maximizing device volume and drug payload, while minimizing the bend radius required to transition between the collapsed and expanded configurations.

When the controlled release device is molded as a single component, one or more protective coatings, each of which may be of different thicknesses, may be applied to the linkages to protect each linkage from hydrolytic degradation, allowing for the release of certain arms at different specific times. Protective coatings of different thicknesses may also be applied to the arms themselves, augmenting or delaying release as the coating degrades. When the linkages or arms are formed separately, different PGS chemistries may be employed to achieve different erosion rates, such as, for example, altering the glycerol:sebacic acid ratio of the starting PGS resin, altering the molecular weight of the starting PGS resin, altering the crosslinking density of the thermoset elastomer, or altering the curing chemistry of the thermoset elastomer. As such, the tunable PGS chemistry permits a very versatile process to form a crosslinked PGS controlled release device.

In some embodiments, the thermoset PGS-based parts are molded separately and weldable to each other using a PGS-based adhesive as a tie coat. In some embodiments, a process includes switching feed streams between different formulations during injection molding to achieve a device containing multiple formations in discrete zones. In some embodiments, different regions of the mold are filled with different chemistries prior to curing to enhance the bonding between different zones without the need for an adhesive.

In some embodiments, the PGS formulation or PGS crosslinking profile includes chemistries that are responsive to acidic environments that accelerate degradation, such as, for example, an acid-labile linker like hydrazone, where the hydrazone:urethane crosslink ratio is preselected in order to tune the degradation rate. In some embodiments, other acid-sensitive crosslinkers and/or controlled release compound tethers, such as cleavable peptide sequences or chemical bonds that dissociate at low pH, are used in addition to or in conjunction with hydrazine for the conjugation.

It will further be appreciated that the devices may be coated after formation. In some embodiments, the molded part may be coated in post-processing, for example using spray coating or dip coating to apply unloaded polymer, drug-loaded polymer, or other controlled release compound-polymer formulation. In some embodiments, a process includes coating a controlled release device with PGSU using a spray coater equipped with a dual-feed nozzle, where the coating solution is composed of 1% to 20% w/w PGS solution in organic solvent, and the coating solution may or may not contain controlled release compound in solubilized form. In another embodiment, a controlled release device is coated with PGSU using dip coating, where the coating solution is composed of 5% to 60% w/w PGS solution in organic solvent, and the coating solution may or may not contain controlled release compound in solubilized or crystalline form. A core-sheath geometry, where the PGSU sheath is unloaded and core is drug-loaded PGSU, reduces burst release from the core. This is because the impermeable PGSU coating prevents contact between the controlled release compound loaded in the core and the external aqueous environment, until the coating has partially or fully degraded to allow passage and release of the drug. A core-sheath geometry, where the sheath is controlled release compound-loaded, permits dual delivery of different controlled release compounds, one from the core component and one from the sheath component, at different rates if desired, by adjusting PGSU parameters such as crosslinking, geometry, and coating thickness.

Once formed, the controlled release device having its pre-determined expanded shape is compressed for insertion into a delivery vehicle to form a delivery system that can be ingested or otherwise transported to a target location within the body.

Figure 10:
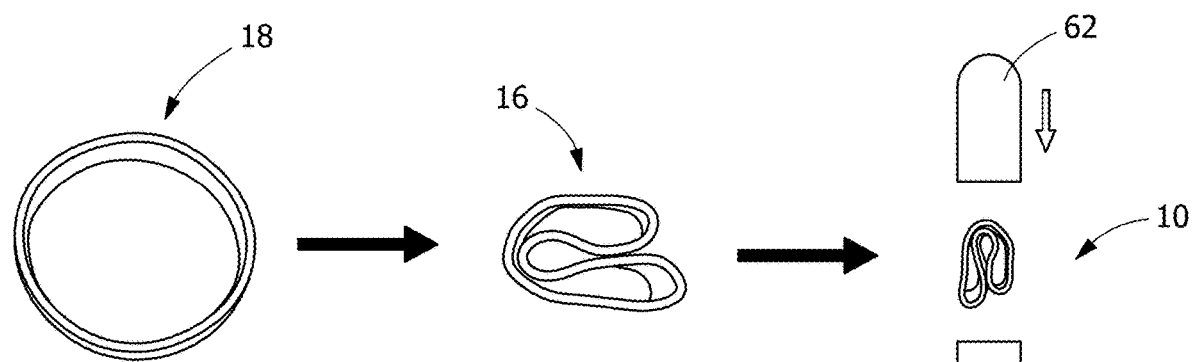
FIG. 10 illustrates formation of a controlled release device delivery system in accordance with another aspect described herein.

For devices in the form of a ring or loop in the expanded state 18, the controlled release device may be flattened or twisted into a double helix for the contracted state 16 as seen in FIG. 9. Similarly, a rod, spiral or helix may be bent or further coiled to its contracted state. FIG. 10 illustrates a contracted controlled release device 16 that is folded, which may be a particularly advantageous contracted state 16 for a ring with a rectangular cross-section that has a width greater than the thickness. It will be appreciated that folds and twists may optionally be used in combination to achieve the contracted state 16.

The approach to contracting or compressing the device for loading into the delivery vehicle may vary slightly depending on the expanded conformation of the controlled release device for successful loading into a capsule without fracture to form the delivery system. Some device conformations may undergo a twisting or torsion motion into the contracted state, while other device conformations may undergo a folding or bending motion into the contracted state. Other device conformations may employ a combination of twisting and folding. Some formulations and shapes may be more amendable to torsional forces, while other formulations and shapes may be more amenable to flexural forces. In addition, controlled release devices that undergo twisting for compression into the contracted state may exert an axial outward force when inside the delivery vehicle, while devices that undergo folding may exert a radial outward force when inside the delivery vehicle. The forces that the controlled release device applies to the inside of the delivery vehicle may have implications on performance during use, stability, and storage of the fully enclosed device.

For example, an outward radial force may be preferred over an axial force, in order to keep the two halves of the capsule locked together and closed, especially over time during shelf storage. In contrast, an outward radial force may cause higher risk of capsule cracking over time. The exerted forces may be formulation-dependent and/or shape-dependent. The exerted forces may also impact long-term stability, such as through residual stresses that may be experienced inside the device, which can lead to undesirable effects like stress relaxation or creep. The exerted forces may also impact how well or how quickly the device elastically springs back to shape upon deployment when in use.

After or during compression of the controlled release device, the contracted controlled release device is processed to temporarily retain the device in that compressed formation for delivery. Again referring to FIG. 9 and FIG. 10, in some embodiments, the contracted controlled release device 16 is inserted into a first capsule half 60 of the delivery vehicle, then placing the other capsule half 62 of the delivery vehicle to close the capsule, stowing the contracted controlled release device 16 therein to form a delivery system 10 for ingestion. Placement in the capsule halves 60, 62 may be by manual manipulation or may use automated equipment similar to that used for metering and dispensing powder into such capsules.

The delivery vehicle for the controlled release device maintains the controlled release device in a contracted or collapsed state prior to delivery to a target location but permits the controlled release device to convert quickly to the three-dimensional (3D) expanded state upon reaching the target location. Appropriate delivery vehicles include, but are not limited to, a non-gelatin capsule, a hard-shelled gelatin capsule, a soft-shelled gelatin capsule (gelcap), a caplet, a tablet, a coating, a food, a feed construct, or a film. In one aspect, size 000 hard-shelled gelatin capsules are the preferred capsule size and type for human adults, although smaller capsules are also possible, to allow easier swallowing, such as size 00 or size 0 capsules. It will be appreciated that the corresponding controlled release device may need to be smaller to in turn fit within the capsule.

The delivery vehicle may provide temporally-delayed, immediate, extended, pulsatile, or ultra-long-lasting release. That is, in addition to the release achieved by the controlled release device, the delivery vehicle can also be engineered to itself expose the controlled release device at a predetermined point in time. As noted, for embodiments in which the deployment is to be within the stomach, the time is likely to be quicker so that deployment can occur prior to the delivery vehicle passing from the stomach into the intestine.

The delivery vehicle may have a pH-dependent degradation to allow for disintegration and timed release in the acidic stomach or basic intestine. Appropriate compositions for the delivery vehicle may include, but are not limited to, gelatin, cellulose, an Eudragit® polymer (Evonik Rohm GmbH, Darmstadt, Germany), starch, sugar, PGS, PGSU, PGSA, or PEG. The delivery vehicle may also contain a controlled release compound for dual drug delivery and differing release kinetics.

In some embodiments, the delivery vehicle includes a PGS-based coating on a conventional oral dosage form, such as, for example, a tablet, a caplet, a capsule, or a gelcap (softgel). Such coatings may be selected to provide pH-dependent degradation and drug release, for timed and targeted delivery customized to the pH conditions of different zones of the gastrointestinal tract, such as, for example, the stomach, the small intestine, or the large intestine. For example, the API may be targeted for the small or large intestine, requiring the device to survive the gastric environment, or vice versa.

In exemplary embodiments, a delivery vehicle includes a PGS, PGSU, or PGSA protective coating, gelcap, capsule, or embedding applied to or around a bulk degrading polymer, such as, for example, PGA, PLA, PLGA, PCL, or PEG, to prolong its lifetime and assist controlled release. This secondary PGS-based layer may or may not be loaded with a controlled release compound.

In some exemplary embodiments, a method includes forming or casting a gelcap (softgel) directly around the controlled release device, which may take advantage of conventional gelcap molding and welding manufacturing processes. In exemplary embodiments, the pre-formed controlled release device is fitted and placed inside an open-face mold, and liquid is poured or flowed over top to form the gelcap within that mold cavity.

In some embodiments, the controlled release device is contained entirely within one half of the gelcap such that the other half of the gelcap does not contain the controlled release device, and the two halves are fused together using heat, pressure, or another form of energy for sealing the two halves. In other embodiments, the controlled release device spans both halves of the gelcap, where one half is molded first. The controlled release device protrudes beyond the first half, and the second half is molded secondarily around the exposed controlled release device.

In exemplary embodiments, the pre-formed controlled release device is fitted and placed inside a closed two-part mold, with holes in the mold to flow in or inject liquid to form the gelcap. Conventionally, gelcaps are formed using two ribbons of flexible material that each make up one half of the outer shell, into which liquid material is filled. In exemplary embodiments, the pre-formed controlled release device is fitted and placed on the ribbon or inside the shell, prior to convergence of the two ribbons for liquid filling, followed by sealing with heat and/or pressure. In some embodiments, the pre-formed controlled release device is shot or pushed in between the ribbons or into the two shell halves at the liquid filling step.

In exemplary embodiments, the controlled release device is not yet solidified, and it is formed by injecting the controlled release liquid formulation into the gelcap shell halves during liquid filling. Internal architecture within the pre-formed gelcap shells may act as a mold to create a controlled release device shape that readily springs open once the gelcap dissolves.

Figure 11:
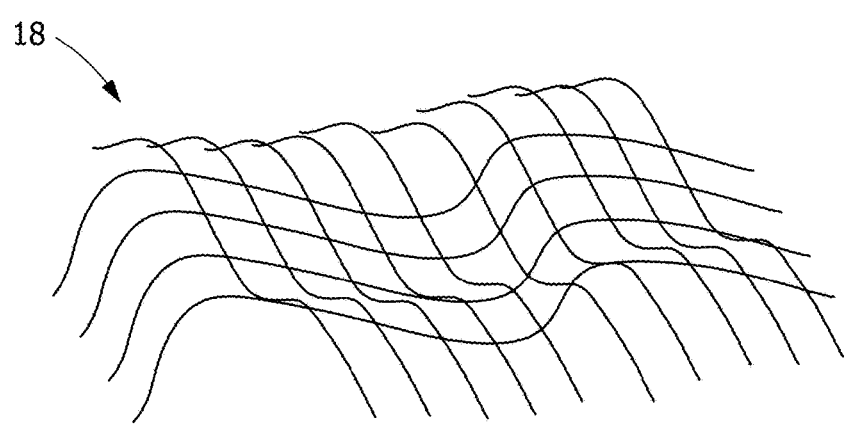
FIG. 11 illustrates a fiber lattice controlled release device in accordance with an aspect described herein.

In some embodiments, the delivery system includes one or more fibers, which may be part of the controlled release device or the delivery vehicle. The fiber material may be biodegradable or non-biodegradable. The fibers may be loaded or infused with a controlled release compound or free of controlled release compound. The fibers may be bound together at a central nucleus or at multiple joints. The fibers may be woven, knitted, or braided into a textile construct. The textile construct can have a variety of architectures and pore structures. FIG. 11 show an example of a lattice of fibers as an expanded controlled release device 18 that can be compacted for insertion into a delivery vehicle.

In some embodiments, the delivery system includes one or more textiles, which may be part of the controlled release device or the delivery vehicle. The textile material may be biodegradable or non-biodegradable. The textile fibers or yarns may be loaded or infused with a controlled release compound or free of controlled release compound.

Figure 12:
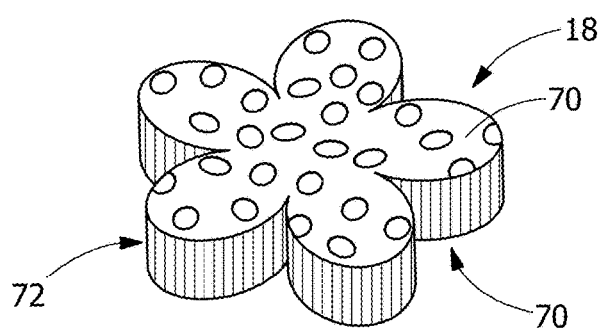
FIG. 12 illustrates a multi-lobed controlled release device in accordance with an aspect described herein.

In exemplary embodiments, a controlled release device includes a textile geometry that is foldable, collapsible, twistable, or compressible, and then springs back by unfolding, untwisting, and/or expanding. Appropriate two-dimensional (2D) and 3D geometries may include, but are not limited to, origami 2D and 3D designs, Hoberman structures, Bucky ball structures, flower shapes with petals for increased surface area, parachutes, umbrellas, wings, stars, wheels, rings, spirals, spheres, cones, ovals, disks, multi-faceted 3D shapes, multi-faceted compressible 3D surfaces (as shown in FIG. 12), compressible spacer fabrics between textile sheets, components, and/or struts, pentagonal pyramids with foldable wings, multi-layered textile sheets with sheets of different rigidity and/or thickness to aid folding and unfolding, or other textile geometric designs that are collapsible and expandable.

In exemplary embodiments, a controlled release device includes textile fibers having shaped and/or multi-lobe cross-sections and/or extensions. Referring to FIG. 12, in one embodiment a compressible three-dimensional textile expanded controlled release device 18 is provided and which can be created without thermoforming. In this embodiment, the textile device 18 is a knitted double needle bar spacer fabric having two faces 70 and one connecting layer 72 formed by machine to have high compressibility characteristics. The connecting layer 72 is formed of a resilient monofilament or multifilament yarn that structurally maintains a certain distance between each face, creating an interlocking layer in the z-dimension. In some embodiments, the z-direction connecting layer 72 is compressed, and once released, mechanically springs back into the original knitted structure. In some embodiments, the z-direction open space is filled with PGSU or another elastomeric compressible polymer. The z-direction yarn enables the compressibility of the controlled release device to a contracted state.

The outer faces of the textile device 18 may be made from a texturized multifilament yarn, chenille, or boucle, enabling the surfaces of the textile to have protruding soft fibers that serve as a mucoadhesive within the stomach.

In exemplary embodiments, a controlled release device includes textile yarns made of fibers with shaped cross-sections to augment and control wicking by capillary action and swelling, due to the space formed between shaped fibers when packed together in the yarn, thus controlling fluid uptake and consequent degradation, surface erosion, swelling, and drug release kinetics of the controlled release device.

In some embodiments, a controlled release device includes textiles formed with biodegradable fibers, such as, for example, fibers made of PGS, PGSU, or PGSA elastomeric thermosets. In other embodiments, biodegradable fibers are made of a PGSU core with an alginate sheath, in which the alginate may be present or alternatively the alginate acts as an initial processing support but is later removed. In other embodiments, a controlled release device includes biodegradable fibers and textile constructs made of individual fiber PGA, PLA, PLGA, PCL, or PEG thermoplastics. In another embodiment, the textile constructs are designed from a "multiplex" yarn, whereby the bundle of yarn fibers are mixed and co-extruded as a single yarn. Such a multiplex yarn with, for example, fifty-six fibrils per yarn is produced to have a mix of yarn fibrils including fast, intermediate, and long-term degradation profiles. Such a yarn or yarns provides temporal and integrity options for the textile including the integration of rapid and controlled release. For example, a multiplex fifty-six filament yarn may have a mixed polymer filament composition of PGS, PGA, PLA, and PLGA to maintain integrity over a period of controlled release rather than designing a textile with multiple independent yarns to achieve the construct.

The multiplex yarn may include bundles of mixed biodegradable and non-degradable fibrils. In exemplary embodiments, a delivery vehicle includes non-biodegradable fibers and textile constructs made of polyethylene terephthalate (PET) or polypropylene (PP) thermoplastics, which are safe and flexible enough to pass through the gastrointestinal tract. The multiplex yarn may simultaneously include degradable and non-degradable polymer fibrils. The non-degradable polymers may be PP or polyethylene (PE), similar to the polymer fillers conventionally used in animal feeds. In exemplary embodiments, a controlled release device includes combinations of biodegradable and non-biodegradable textile components such as PP and PE, which may, for example, break down into flexible textile pieces within the stomach and eventually pass through the bowel. In exemplary embodiments, a delivery vehicle includes thermoplastic fibers and textile constructs coated with PGS, PGSU, or PGSA as a composite structure. The thermoplastics may be formed into three-dimensional textile constructs by, for example, non-woven, weaving, knitting, or braiding.

In exemplary embodiments, the thermoplastic textile drives the shape transformation of the end component by employing shape setting techniques. In exemplary embodiments, the three-dimensional structures are heat set, thermoformed, or welded into more complex and more voluminous geometries, such as, for example, a shape set onto tapered mandrels or step-down geometry mandrels or other mold shapes. In exemplary embodiments, these shape-set textile constructs are collapsed down into small dimensions for delivery through small openings, such as, for example, for insertion through a catheter, for packaging into an oral capsule, or for insertion through an orifice into a bioprocessing containment vessel for bioprocessing. After being constricted down, the deployed construct springs back to its set shape once that constrictive force is removed, such as, for example, through disintegration of the oral capsule or removal of a guiding catheter. In exemplary embodiments, a woven, braided, or knit structure is formed into a complex three-dimensional shape in the relaxed state and is compacted down into a delivery system and then recovers to its functional shape after deployment.

In some embodiments, a delivery system includes PGSU fibers or filaments that are intertwined, where some fibers or filaments have different crosslinking densities and/or contain different controlled release compounds. The fibers or filaments may also have a core-sheath design for dual drug delivery and variable release kinetics. The fibers or filaments may also have unique architectural cross-sectional geometries, beyond the conventional "Euclidian" circle-cylinder, such as, for example, a square, an asterisk, a plus-sign, an H-shape, or a multi-lobal shape, to achieve different surface areas and surface area-to-volume ratios, to augment surface erosion controlled release compound release. The strands may be long and may be folded and packaged into an oral capsule, gelcap, caplet, or tablet, so that they expand back into long strands once inside the stomach for a predetermined residence time anywhere from hours to days or weeks.

In exemplary embodiments, a delivery vehicle includes polymer-coated or polymer-infilled textiles, actuating polymeric shape recovery with stimulation, such as, for example, through temperature, pH, enzyme binding, hydrogel formation, or other stimulus, to create shape-retentive three-dimensional textile-based structures.

In exemplary embodiments, a controlled release device includes a thermoplastic-based textile structure that is further cut, such as, for example, by heat, laser, ultrasound, or radiofrequency (RF), into a complex shape including multi-lobe designs with varying numbers of appendages and smooth edges for optimized residence attachment.

In exemplary embodiments, a delivery vehicle includes composite structures of PGS-based coatings on PGS-based or non-PGS-based textiles. The coatings may be loaded or infused with a controlled release compound or free of controlled release compound.

In exemplary embodiments, a delivery system includes PGS-based particles that are formed as described in U.S. Pat. No. 10,556,217, issued Feb. 11, 2020, incorporated herein by reference. In exemplary embodiments, the delivery vehicle includes PGS-based microspheres with a diameter less than 1 mm. In exemplary embodiments, the delivery vehicle includes PGS-based nanospheres with a diameter less than 1 µm. In exemplary embodiments, the delivery vehicle includes PGS-based beads with a diameter less than 1 mm. Such spheres may be housed within a conventional oral dosage form or may alternatively be in a liquid formulation. Such spheres may have different degrees of cross-linking, pH-dependent degradation, and drug release, for timed delivery to different zones of the gastrointestinal tract, such as the stomach, different regions of the small intestine, and different regions of the large intestine.

In some embodiments, the delivery system includes PGSU or any other PGS-based microspheres or beads coated with polymers for tunable release profiles and degradation rates. Coating may include but are not limited to, PGS, PGSU, chitosan, hyaluronic acid, dextran, or Eudragit® polymer (Evonik Rohm GmbH, Darmstadt, Germany). The coating may or may not contain a controlled release compound. Coating processes may include but are not limited to fluid bed coating, pan coating, or spray coating.

In some exemplary embodiments, the delivery system includes PGSU or other PGS-based microspheres loaded into a capsule alone or in combination with an expandable controlled release device. Upon release from the capsule, the microspheres may float in the gastric fluid, increasing gastric retention time and allowing controlled release of the controlled release compound. To achieve floating, PGSU microspheres can be fabricated with a degree of hydrophobicity, surface tension, or propensity for self-aggregation so that microspheres clump together at the liquid-gas interface to form a floating raft. The microsphere aggregation may contain gas trapped between the microspheres that aids floating. Microsphere size can be selected to aid this behavior, such as, for example, microspheres with less than 0.1 mm diameter tend to aggregate and float to the water-air interface. Microspheres can be uniformly crosslinked throughout or crosslinked with a core-shell structure. The controlled release compound may be loaded into core, shell, or homogeneously within the microspheres. Alternatively, to achieve floating, PGSU microspheres can be fabricated to be hollow or porous. The manufacturing techniques for hollow microspheres may include, but are not limited to, emulsion-solvent diffusion, emulsion-solvent evaporation, spray drying, precipitation, phase separation-coacervation, or spheronization methods. The controlled release compound may be loaded in the shell of the microspheres. The shell of the microspheres may have different degrees of crosslinking, different thicknesses, and different loadings of the controlled release compound.

In some exemplary embodiments, appropriate delivery vehicles for the microspheres or beads may include but are not limited to capsules, tablets, coatings or hydrogels. The delivery vehicles may contain microspheres of different sizes, different crosslinking, containing different controlled release compounds, different drug loadings, different polymers, crosslinked throughout or core-shell microspheres to obtain desired release profile, degradation rates and subsequent removal from the gastrointestinal tract.

The crosslinked PGS used in thermoformed or textile embodiments may be composite PGS that includes a filler of a PGS-based cryomilled particulate flour that may be cured to different degrees of crosslinking, such as described in U.S. Pat. No. 10,525,140, issued Jan. 7, 2020, incorporated herein by reference. In some embodiments, a process includes creating a PGSU composite, where PGSU filler created by cryomilling is mixed into the PGSU device using PGSU as a binding matrix. The filler and the matrix may contain the same or different controlled release compounds. The filler and the matrix may contain the same or different crosslinking densities. The degradation rate of the binding matrix controls the breakdown of the composite into particles small enough to pass into the intestinal tract. In exemplary embodiments, the PGS-based filler is spheronized into smooth microspheres by, for example, phase exclusion viscoelastic thermal sphericalization, microwave radiation, or a solvent etch process.

In one embodiment, a delivery vehicle includes a PGS-based coating, a PGS-based flour, and a PGS-based sphere co-molded with a gastroretentive device.

In exemplary embodiments, a delivery vehicle includes erodible PGS filler and/or PGS-based spheres that are embedded in an erodible PGS-based binding matrix and that are released after matrix degradation. In exemplary embodiments, the binding matrix controls the degradation rate, thereby controlling breakdown of the composite material and release of PGS filler particles and hence permitting passage into the intestinal tract.

In some embodiments, a delivery vehicle includes PGS-based forms that initially swell, rather than elastically returning to an expanded state, to a size large enough to stay in the stomach for an extended amount of time. In some embodiments, a delivery vehicle or controlled release device includes PGSU or any PGS-based polymer containing a swelling agent, such as, for example, PEG, alginate, or gelatin. In some embodiments, a process introduces pores into the polymer during manufacturing to enhance swelling and water uptake once deployed, such as by inclusion of porogens, blowing agents, pneumatogens, or by a foam process. In such embodiments, the composition swells after consumption to a size large enough to remain in the stomach for an extended period of time. In some embodiments, the swollen material maintains mechanical integrity during its degradation. In some embodiments, the swellable portion of the delivery vehicle makes up the core or sheath in a core-sheath design. In some embodiments, the swellable portion delivers the controlled release compound at a controlled rate.

Some embodiments may also incorporate PGS filler as a flour in a tablet compression manufacturing process. In exemplary embodiments, the elastomeric flour provides benefits during tablet compaction that may include, but are not limited to, compressibility, binding, or lubrication. The elastomeric flour may be loose or blended with other excipients. In exemplary embodiments, the elastomeric flour is used in animal feed. PGS and API formulated microparticle flour may be compression co-processed or dry blended with food and feeds such that the PGS acts as a binding agent or flow control agent to the raw feed processing to final form. Such an incorporation acts both as a binder or flow agent and as a controlled release polymer embedded within the feed particle structure. Such compression structures may include multiple geometries, temporal digestion profiles and the ability to incorporate prodrug components that combine or interact in vivo. PGS flour has anti-bacterial properties that may extend the shelf life and use life of animal feed, offering fouling resistance to the feed to insure animal health.

In exemplary embodiments, a controlled release device includes PGS-based beads, microspheres, or nanospheres that are contained in a tablet, caplet, gummy, capsule, or gelcap for oral consumption and that self-aggregate once inside the stomach. In some embodiments, an applied coating causes the self-aggregation. In some embodiments, the applied coating may become sticky when wetted, such as, for example, by formulating a polysaccharide, such as, for example, xanthan gum, gum arabic, gelatin, or alginate. In some embodiments, the surface chemistry and/or the surface roughness causes aggregation, such as, for example, a surface that forms strong hydrogen bonding with other beads, microspheres, or nanospheres. In some embodiments, the aggregation is pH dependent. In some embodiments, the aggregation is driven by hydrophilic-hydrophobic repulsion. In some embodiments, the aggregation is triggered by enzymes in the saliva during mastication. In some embodiments, the aggregation is triggered by released bloomed additives, glycerol, sebacic acid, or PGS oligomers. In some embodiments, the aggregated material has mechanical integrity during degradation.

In exemplary embodiments, a controlled release device includes a PGS-based hydrogel in the form of a 3D structure, such as, for example, a ring, a star, a wheel, a coil, a sphere, beads, microspheres, nanospheres, or other aforementioned shape that is contained in a gelatin capsule for oral consumption. In exemplary embodiments, the hydrogel swells after consumption to a size large enough to remain in the stomach for an extended amount of time. Alternatively, or in conjunction, the delivery vehicle may aggregate into a swollen mass to provide retention. In some embodiments, the swelling triggers aggregation. In some embodiments, the swelling is pH dependent. In some embodiments, the swelling is triggered by enzymes in the saliva during mastication. In some embodiments, the swelling releases bloomed additives, glycerol, sebacic acid, or PGS oligomers that cause aggregation. In some embodiments, the swollen material has mechanical integrity during degradation. In some embodiments, the swellable portion of the delivery vehicle makes up the core or the sheath in a core-sheath design. In some embodiments, the swellable portion delivers the drug at a controlled rate.

In exemplary embodiments, such swellable designs are useful for ruminant animals such as cattle, where the food bolus travels through four stomachs and is masticated twice. After processing in the rumen, the food travels to and is processed in the reticulum. The food then travels up the esophagus for the second mastication followed by travel back down the esophagus to the omasum, the abomasum, and finally into the intestine.

In some embodiments, the swellable nature provides additional retention in the rumen and reticulum initially and then provides a significantly increased volume for a second mastication, where the material is broken down further into smaller portions for further release in the omasum and abomasum. In some embodiments, a non-swelling PGS binding matrix is masticated and delivers drug during residence in the rumen and reticulum, and upon a second mastication exposes previously-protected PGS microspheres to water and gastric fluids. In exemplary embodiments, the exposed PGS microspheres then expand, aggregate, swell, and/or degrade, with or without gastric retention, releasing the same or a different drug into the omasum, the abomasum, and the downstream intestine. In some embodiments, a method includes layering a PGSU hydrogel and cellulose-based material, in which the PGSU hydrogel is loaded with one or more controlled release compounds. In such embodiments, the ruminant animal digests the feed more than once, allowing the delivery vehicle to release controlled release compound in different stomach compartments during multiple digestive cycles. In exemplary embodiments, the delivery vehicle is ingested and chewed and travels to the rumen. In exemplary embodiments, the cellulose-based layer is digested in the rumen and reticulum, exposing the next PGSU hydrogel layer, allowing it to swell and release its controlled release compound until the delivery vehicle travels back to the mouth. The delivery vehicle is masticated again and travels to the omasum where the next cellulose layer is digested, and the PGSU hydrogel beneath it is exposed for swelling. In exemplary embodiments, the number of rumination cycles is controlled by the number of layers of PGSU hydrogel and cellulose.

In exemplary embodiments, the delivery system includes a mucoadhesive design, where the mucoadhesive nature provides additional retention of the controlled release device. Textile geometries may include a pile structure, such as, for example, a velour or a double-needle bar that is cut down the center which serves as a mucoadhesive to the gastric mucosa.

In exemplary embodiments, a delivery vehicle includes an edible textile design with a velour surface texture, where the material is masticated and ingested initially, and the velour surface adheres to the tissue linings of the rumen and reticulum for enhanced retention. Then upon the second phase of mastication, the textile design is broken up into further smaller components that are still mucoadhesive, or alternatively the second mastication reveals new mucoadhesive regions, either through chemical or mechanical means, so that there is still enhanced retention in the omasum and abomasum.

In some embodiments, a parenteral delivery includes the controlled release of antigens from a delivery vehicle in the parenteral space, over a period of time, such as, for example, 4-6 weeks, as an alternative to a conventional vaccine injection or compressed biomass formulation. In some embodiments, the delivery vehicle includes a formulation with a hydrophobic ingredient, such as, for example, beeswax, to resist water attack and/or control water uptake and consequent hydrolytic degradation, surface erosion, and drug release kinetics. In some embodiments, the delivery vehicle includes a multi-layered construct, alternating between controlled release compound-loaded PGSU and beeswax layers. In such embodiments, the first PGSU layer degrades through surface erosion and releases its drug payload, but the underlying beeswax layer provides a hydrophobic barrier, halting water ingress and water access to the remaining portions of the delivery vehicle, thus providing a pause or stall in drug release. After some time, once the beeswax breaks down, the next controlled release compound-loaded PGSU layer is exposed and begins to release its drug payload, which may be either the same or a different controlled release compound. As such, such a delivery vehicle achieves pulsatile release. In some embodiments, the delivery vehicle is placed in the parenteral space to deliver vaccines and subsequent vaccine boosters, achieving the sometimes-requisite multi-week spacing between vaccine boosters.

The delivery system may provide controlled release for any relevant therapeutic field, such as, for example, infection, inflammation, immunoinflammation, arthritis, pain management, opioid dependence, human immunodeficiency virus (HIV) prevention, HIV treatment, contraception, oncology, dementia, Alzheimer's, Parkinson's, bipolar disorder, depression, anxiety, attention deficit hyperactivity disorder (ADHD), schizophrenia, psychosis, erectile disfunction, diabetes, obesity, ophthalmology, diet supplementation, weight gain, or gut microbiome health. In most cases, these ailments may be treated through oral administration. In some cases, these ailments may require localized administration, such as, for example, intraocular, intrauterine, or intravaginal delivery.

In exemplary embodiments, the PGS-based polymer includes a high sebacic acid content, by tuning the glyercol:sebacic acid ratio, for the treatment and maintenance of diabetes. Medium-chain dicarboxylic acids are a promising alternative energy substrate in diabetes nutrition, energy utilization, metabolism, and therapy. Oral delivery of dicarboxylic acids like sebacic acid has successfully improved glycemic control in animals and humans with type II diabetes, likely by enhancing insulin sensitivity, and has reduced hepatic gluconeogenesis and glucose output. Moreover, bipolar disorder is a known comorbidity with type II diabetes, and one common anti-convulsive drug for bipolar disorder is the fatty acid, valproic acid. In some embodiments, the delivery vehicle includes a formulation of PGS that enhances, optimizes, or supports delivery of sebacic acid. Such a device may alternatively provide sebacic acid (and/or controlled release compound) delivery by direct gastric feeding to infants or dysphagic, unconscious, compromised, or traumatically-injured patients.

In exemplary embodiments, the delivery vehicle provides controlled release to treat a gastrointestinal disease, such as, for example, short bowel syndrome, Hirschsprung disease, or irritable bowel syndrome.

In exemplary embodiments, the delivery vehicle provides controlled release for contraception in humans and animals, such as, for example, for estrus control, fertility management, animal husbandry, or sterilization.

In other embodiments, a flexible controlled release device provides controlled release for ex vivo bioprocessing products. Such applications may include a controlled release device inside a bioprocessing containment vessel. Bioprocessing containment vessels include, but are not limited to, polymer bags, blood and fluid collection, storage, and delivery bags, bioreactors, bioreactor liner bags, cartridges, mesenchymal stem cell (MSC) expansion or differentiation systems, chimeric antigen receptor T cell (CAR-T cell) expansion, activation, transduction, or transfection systems, or flow-through systems. Controlled release devices housed in these bioprocessing containment vessels may similarly benefit from designs and geometries that are compressible, deliverable through a small orifice, and expandable once inside the bioprocessing containment vessel. The large, expanded shape similarly prevents the controlled release device from washing away or flowing through prematurely during bioprocessing.

Bioprocessing containment vessels frequently have multiple ports for sampling, air inlet, air outlet, filters, check valves, fluid transfer, couplings, fittings, tubing, Luer locks, caps, and plugs. In some cases, a sampling port is the appropriate orifice through which to introduce the controlled release device. Such applications may include, but are not limited to, the delivery of "en-resident" life-cycle or a bioprocessing staged process sequence, whereby cells for treatments, such as activation or transduction, do not have to be removed or transferred from an initial single-use bioprocessing vessel (SUB) to the downstream SUB for continued bioprocessing. For instance, biologics and trophic agents incorporated into an expandable device may be sequentially added to a SUB via the compressible delivery device as a sequential step-wise introduction of active agents and nutritional components.

In exemplary embodiments, a composition for a delivery vehicle includes a hydrogel formulation of PGS, such as, for example, a hydrogel formulation including a synthetic polymer like PEG, or a natural polymer like gelatin, collagen, fibrin, elastin, a proteoglycan, or a polysaccharide like chitosan, alginate, glycosaminoglycans, and/or hyaluronic acid. In exemplary embodiments, a controlled release device includes a hydrogel formulation of PGS that is highly swellable, in the range of 300-500% w/w. In exemplary embodiments, the swellability provides gastric retention as an alternative to shape springback. In some embodiments, a composition contains at least 50% w/w of a multi-armed PEG-based compound, less than 30% w/w of PGS, with a polyol:diisocyanate ratio between 4:1 and 10:1 by mass. In some embodiments, the isocyanate is hexamethylene diisocyanate (HDI).

In exemplary embodiments, a composition for a controlled release device includes a formulation with smaller diacids and multifunctional acids. Preferably these acids are covalently bound to PGS, but a composition formulated using PGS mixed with organic acid in combination with a covalently bound PGS-adduct binder may be favorable. Such acids may include, but are not limited to, citric acid, adipic acid, decanoic acid, stearic acid, myristic acid, or oleic acid. These acids may be included, for example, to further crosslink the PGS material or crosslink it in a shorter amount of time or to provide crosslinks that are more susceptible to hydrolysis in the stomach.

In exemplary embodiments, a composition for a controlled release device includes a formulation with different catalysts, such as those including heavy metals, such as, for example, tin or platinum, and those including acids, such as, for example, citric acid or tartaric acid, and salt forms of acids. These catalysts may be used during the PGSU formation process, catalyzing the reaction between the isocyanate and the PGS resin polyol. These catalysts may also be used to accelerate the PGS polycondensation reaction, during the synthesis of PGS resin or formation of PGS thermoset. These catalysts may also be used in other PGS crosslinking chemistries, producing different reaction kinetics and polymer matrix formulations. Since these catalysts typically remain in the final cured PGS-based dosage form, catalyst concentrations are selected that fall within acceptable limits for safety in vivo.

In exemplary embodiments, a composition for a delivery vehicle or controlled release device includes a formulation for delivery of gases, such as, for example, oxygen, carbon dioxide, or nitrogen. Such gases may be contained within the polymer matrix, either as macro-, micro-, or nano-bubbles. In such embodiments, gas impermeability through the polymer matrix is maintained to contain the gas inside, until the polymer erodes and releases the pockets of gas. In other embodiments, the polymeric device is stored in the same gas that is entrapped such that the gas is at equilibrium on the inside and outside of the device, and the risk of gas leaching is reduced. In other embodiments, oxygen generation from the polymer may be provided via incorporation of a metal peroxide, such as, for example, $CaO_2$ or $MgO_2$. In some embodiments, carbon dioxide is released from a delivery vehicle or controlled release device using bicarbonate formulations.

Such gases may be therapeutic or nutritional when delivered to cells or tissues in the body, in biocontainment, or in a bioreactor. Oxygen is a potent biochemical signaling molecule that also regulates genes during organism development. Oxygen delivery may be used to promote healing, regulate genetic pathways, treat hypoxia, or simply maintain appropriate oxygen levels. Conversely, low oxygen tension is important in a native mesenchymal stem cell (MSC) bone marrow microenvironment. Physiologically-relevant hypoxic conditions of 2-3% oxygen are known to induce MSC proliferation and plasticity compared to the normoxic condition of 20-21% oxygen. Gases or substances that quench, sequester, scavenge, absorb, or react with oxygen may be delivered to MSCs, whether in native in vivo niches or in vitro culture, to lower the oxygen concentration and enhance MSC therapeutic behavior. One example of such substances that bind oxygen are transition metals, such as, for example, cobalt and iron. In one embodiment, the substance is platinum or palladium nanoparticles embedded in the crosslinked PGS matrix. Certain carbon dioxide levels, such as 5% carbon dioxide, are also important to maintain cell viability in certain systems, such as, for example, in bioreactors, biocontainment, or cell culture. Carbon dioxide gas is a byproduct of the PGSU reaction when water is present and becomes trapped in the PGSU network during crosslinking. The intentional addition of water may permit delivery of carbon dioxide or formation of a PGSU foam.

Similarly, delivery of other substances, such as, for example, anti-oxidants or phenols, that scavenge or quench reactive oxygen free radicals, and prevent oxidative stress, is also possible.

In exemplary embodiments, a composition for a controlled release device includes a PGS-based formulation that exhibits anti-microbial performance, which lengthens the shelf life and in-use life of animal feed, for example, by offering fouling-resistance to damp and unsanitary environments.

In exemplary embodiments, a composition for a delivery vehicle includes PGS of varying hydrophilicity or hydrophobicity, which impacts controlled release compound compatibility with PGS, controlled release compound mixing and incorporation into PGS, controlled release compound loading levels achievable within PGS, controlled release compound release from the polymer matrix, and PGS degradation. Varying hydrophilicity or hydrophobicity also impacts shelf life, and fouling-resistance for animal feed. Additionally, different types of animal feed require different levels of dryness or wetness, which may be achieved by balancing the hydrophilic and hydrophobic contributions within a PGS formulation.

In exemplary embodiments, a delivery system includes a PGS-based chewable gummy. In exemplary embodiments, a delivery system includes a PGS-based swallowable gummy. Such gummy products may be an alternative to existing gummy products, such as for vitamin and mineral delivery, but with higher loading, slower degradation throughout the gastrointestinal tract, pH-targeted degradation, delivery to the stomach or intestine, and/or prolonged release kinetics. In another embodiment, crosslinked PGS is used as an ingredient in a chewing gum, to create a chewing gum that is more easily digestible and safer for ingestion. Such chewing gums may have high loading of ingredients for oral delivery, such as sugars, sweeteners, menthol, mint varieties, flavorings, and/or nicotine. Such chewing gums may provide prolonged release kinetics and resistance to enzymatic degradation by saliva.

In exemplary embodiments, a delivery system includes forms that are fabricated entirely or in part using additive manufacturing. Appropriate additive manufacturing methods for the crosslinked PGS may include, but are not limited to, fused deposition modeling, selective laser sintering, material extrusion, bioprinting, stereolithography, digital light processing, digital light synthesis (continuous liquid interface production), inkjet printing, or material jetting, depending on the chemistry, viscosity, and polymerization kinetics. In some embodiments, the entire controlled release device or delivery system is manufactured by additive manufacturing. Changing out printheads during additive manufacturing permits changes to the formulation of the controlled release device partway through the print. For example, distinct zones within the same part may be printed with PGSU of different crosslinking densities, and/or similarly with different concentrations of the controlled release compound.

In some embodiments, a dual-barrel 3D printer combines the PGS-controlled release compound-catalyst blend with HDI right at the nozzle prior to layer extrusion. In some embodiments, the 3D printer is equipped for pneumatically-driven extrusion through a dual-barrel syringe and mixing nozzle tip. In some embodiments, a single barrel 3D printer directs a PGSU formulation with a working time greater than the time needed to print an entire barrel volume, such as, for example, 20 minutes for a 10-cc syringe volume. Fillers, solvents, and/or plasticizers may be included to modify the PGSU formulation viscosity, and controlled release compound incorporation may impact the rheology as well. The additive manufacture of PGSU opens many other possibilities, such as, for example, patient-specific implantable products and designs, complex geometries with internal struts and voids, on-demand manufacturing to reduce the stability testing burden and equipment costs, and multi-material constructs with co-delivery of multiple controlled release compounds having different release kinetics from tuned PGSU formulations.

For example, structures may be formed by additive manufacture to include many complex or intricate winged features to increase surface area and flexibility.

EXAMPLES

The invention is further described in the context of the following examples which are presented by way of illustration, not of limitation.

Example 1

A single-component 2-mm diameter PGSU rod was made using a solvent-free PGS resin (REGENEREZ® resin available from The Secant Group, LLC, Telford, PA) and HDI in a 3.5:1 PGS:HDI w:w ratio via reactive injection molding. The PGS resin and HDI were mixed with a tin catalyst under vacuum and the blended material was then injected into a mold for curing at room temperature. The resulting PGSU rod was found to be sufficiently flexible to bend for insertion into a hard-shelled gelatin capsule in a contracted state. The capsule was disintegrated in simulated gastric fluid (SGF) having a pH 1.2 and a temperature of 23° C. The rod elastically recovered back to its original expanded state.

Example 2

A single-component circular ring was injection molded using the same resin and HDI combination of Example 1. The ring had a 32 mm diameter and a 2-mm circular cross sectional diameter and was sufficiently flexible to twist into a double helix for insertion into a hard-shelled 000 gelatin capsule. The capsule was disintegrated in SGF upon which the ring expanded back to its original expanded state.

Example 3

A single-component circular ring was injection molded in the same fashion as Example 2 except that a 35 mm diameter ring was produced with a 3.5 mm circular cross-sectional diameter and demonstrated sufficient flexibility to be inserted into a gelatin capsule.

Example 4

A ring was made in the same manner and dimensions as Example 3, except that an additional component was added to provide a ring loaded with 50% w/w phenazone. The resulting ring still demonstrated sufficient flexibility to be inserted into a gelatin capsule.

Example 5

Another ring was made in the same manner as Example 4, but with a circular cross-sectional diameter of 2.5 mm. Again, the ring demonstrated good flexibility for insertion into a gelatin capsule.

Example 6

A four point star, as shown in FIG. 5B, having an internal angle 30 of 25° and an external angle 32 of 115°, was created by injection molding a 60% solution of PGS resin (REGENEREZ® resin) in a 50:50 w:w acetone:propyl acetate solvent and HDI at a 3.5:1 PGS:HDI w:w ratio along with phenazone to form a controlled release device having 40% w/w phenazone. The star had a square cross-sectional shape with sides measuring 2 mm. The star shaped controlled release device was folded and inserted into a 000 hard gelatin capsule and placed in SGF, recovering to its original expanded star shape after the capsule dissolved.

Example 7

A thin sheet measuring 20 mm in width, 40 mm in length, and 0.8 mm in thickness was molded using the same formulation as Example 6 at the same loading amount of phenazone. The sheet was rolled into a tube and inserted into a 000 hard gelatin capsule and placed in SGF, recovering to its original expanded sheet form after the capsule dissolved.

Example 8

A 30% solution of PGS resin (REGENEREZ® resin) in a 50:50 w:w acetone:propyl acetate solvent and HDI at a 3.5:1 PGS:HDI w:w ratio combined with micronized lactose were used to mold a 300-μm diameter fiber having 80% w/w lactose. The micronized lactose had a particle size of d50≤5 μm and d90≤10 μm.

Example 9

A star/flower shaped PET textile with collapsible petals as shown in FIG. 12 composed of two faces connected by a double-needle bar spacer fabric was created and compressed into a contracted state for insertion into a hard-shelled gelatin capsule. The capsule was disintegrated in an acidic environment and the textile expanded back to its original expanded state. The diameter of the textile was 30 mm and the thickness was 4 mm.

Example 10

Mass loss and release of a controlled release compound from single-component PGSU rods, loaded with 40% w/w caffeine was quantified throughout a drug release test in simulated gastric fluid at 37° C. Solvent-free compositions at two different PGS:HDI w:w ratios, 3.5:1 (nominal crosslinking) and 2:1 (high crosslinking), were mixed to create two distinct PGSU crosslinking densities. In each case, the rods were otherwise created in the same manner as described in Example 1 by injection molding, but using a mold to produce a rod with a cross-sectional diameter of 3 mm.

Figure 13:
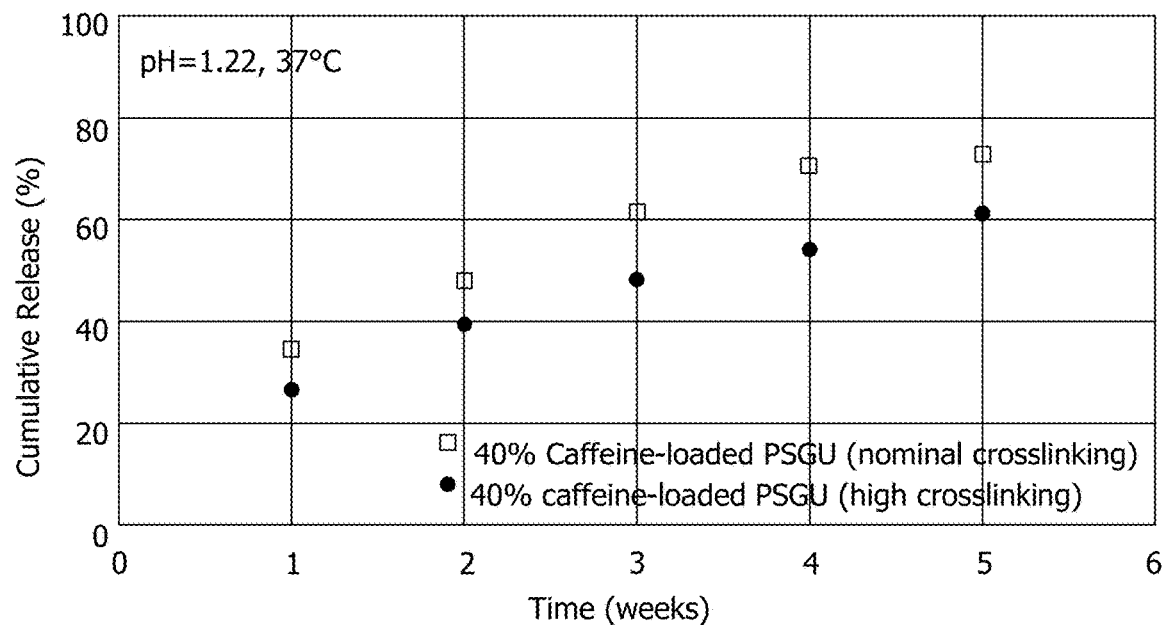
FIG. 13 graphically illustrates API release as a function of time for a controlled release device under acidic conditions in accordance with an aspect described herein.

Cumulative mass loss and caffeine release were determined after one week, two weeks, three weeks, four weeks, and five weeks. The caffeine release data is illustrated in FIG. 13.

Figure 14:
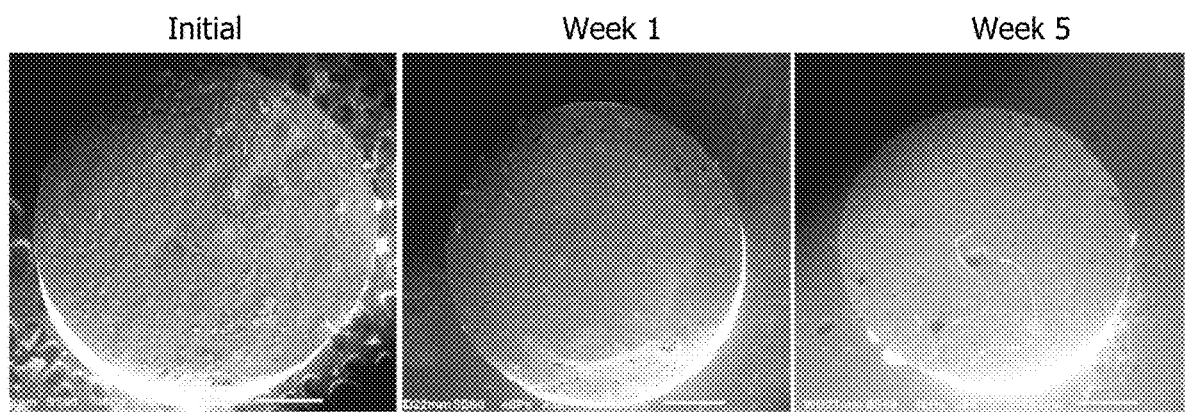
FIG. 14 illustrates degradation over time of a controlled release device under acidic conditions in accordance with an aspect described herein.

Scanning electron microscopy (SEM) images were obtained to show surface degradation of the single-component PGSU rods, loaded with caffeine, at two distinct PGSU crosslinking densities, throughout a drug release test in their initial state and after up to 5 weeks in SGF. FIG. 14 shows SEM images of the high crosslinking rod after zero, one and five weeks in SGF at 37° C.

Example 11

PGSU rods having a cross-sectional diameter of 3 mm were injection molded using both solvated and solvent free compositions at 3.5:1 PGS:HDI w:w to assess mass loss over time in both acidic (stomach) and basic (intestinal) environments. SGF as previously described was used for the acidic environment while a triethylamine solution with a pH of 11.44 was used for the basic environment. Each fluid was heated to 70° C. to accelerate the degradation rate.

Figure 15A:
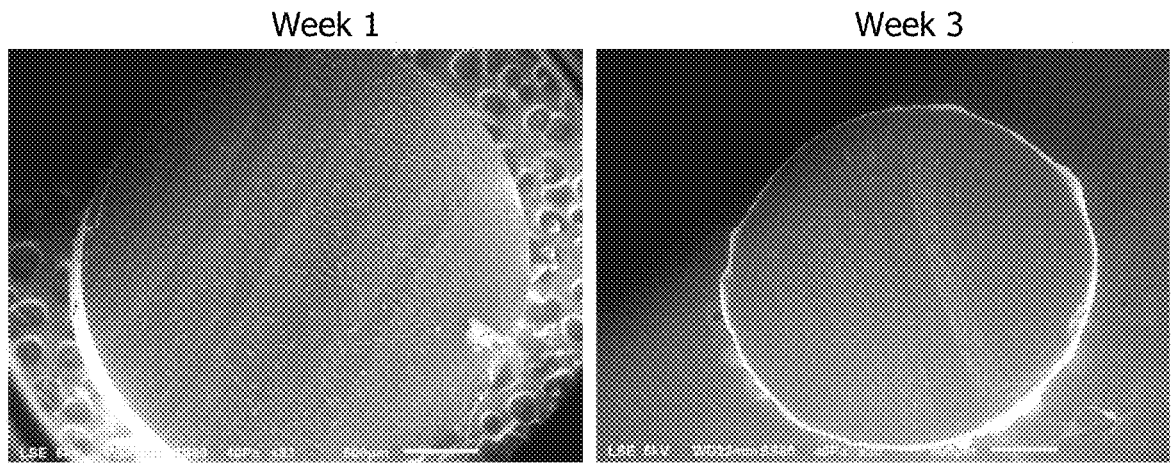
FIG. 15A illustrates degradation over time for a controlled release device under acidic conditions in accordance with an aspect described herein.
Figure 15B:
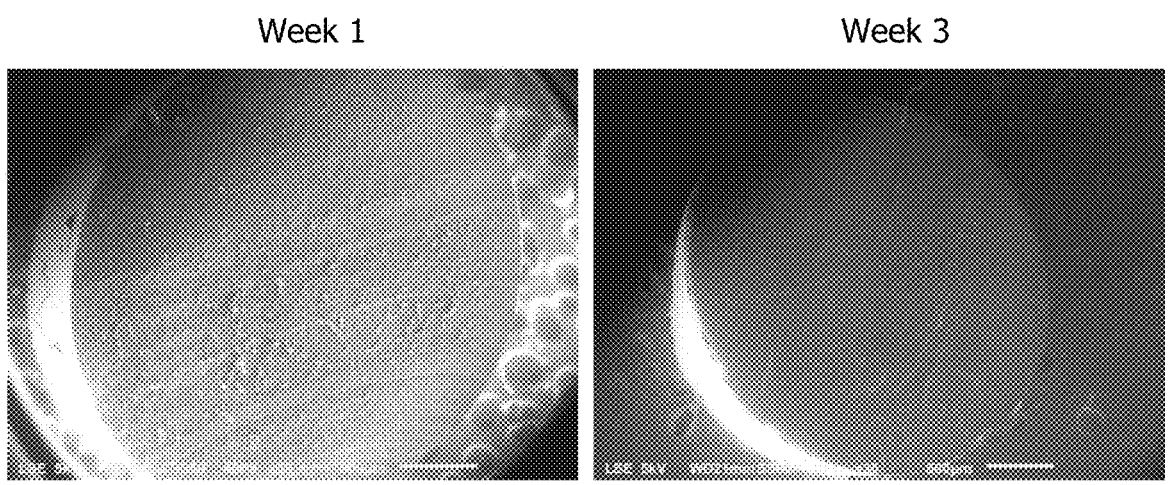
FIG. 15B illustrates degradation over time for a controlled release device under basic conditions in accordance with an aspect described herein.
Figure 16A:
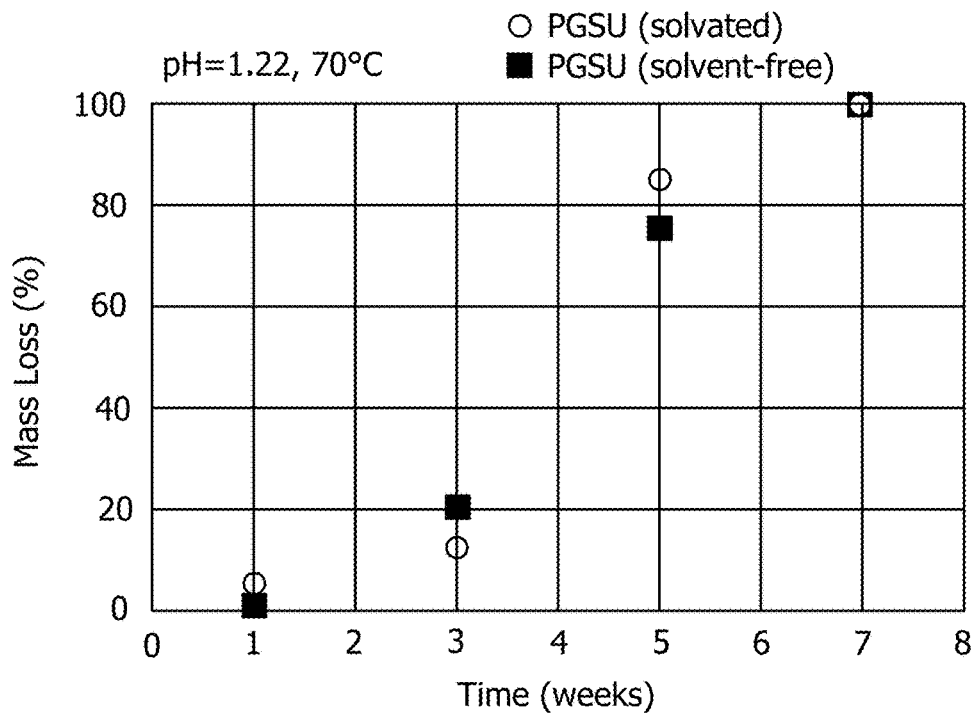
FIG. 16A graphically illustrates mass loss as a function of time for controlled release devices under acidic conditions in accordance with an aspect described herein.
Figure 16B:
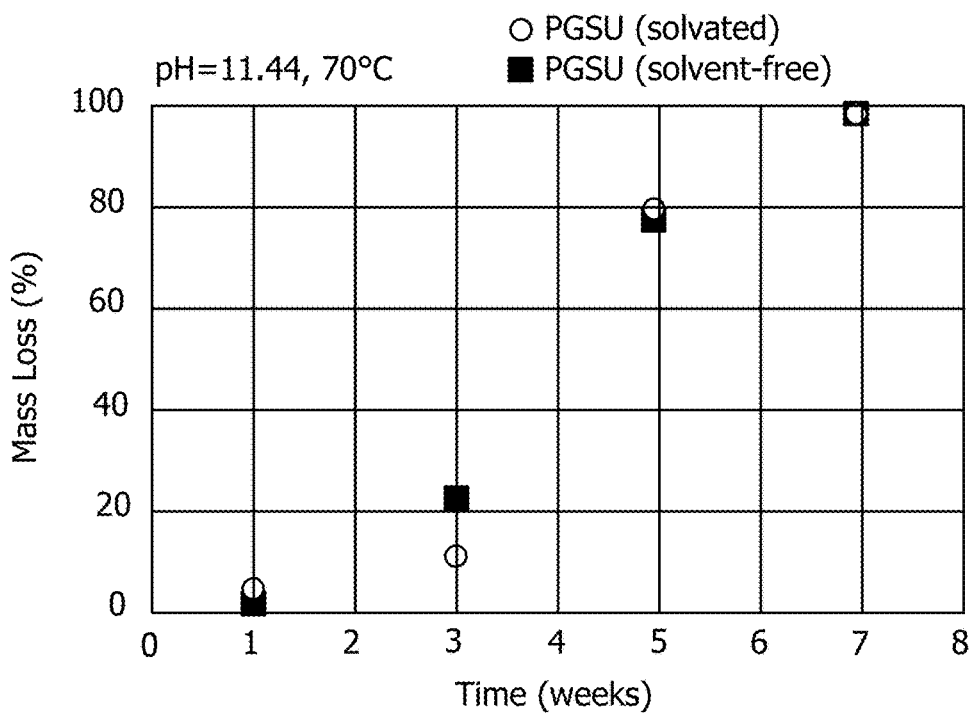
FIG. 16B graphically illustrates mass loss as a function of time for controlled release devices under basic conditions in accordance with an aspect described herein.

FIG. 15A and FIG. 15B are SEMs of the surface erosion seen after 1 and 3 weeks for acidic and basic environments, respectively. FIG. 16A and FIG. 16B graphically illustrate mass loss over time for acidic and basic environments, respectively, with all examples showing 100% mass loss (i.e., complete erosion) between week 5 and week 7.

Example 12

Figure 17:
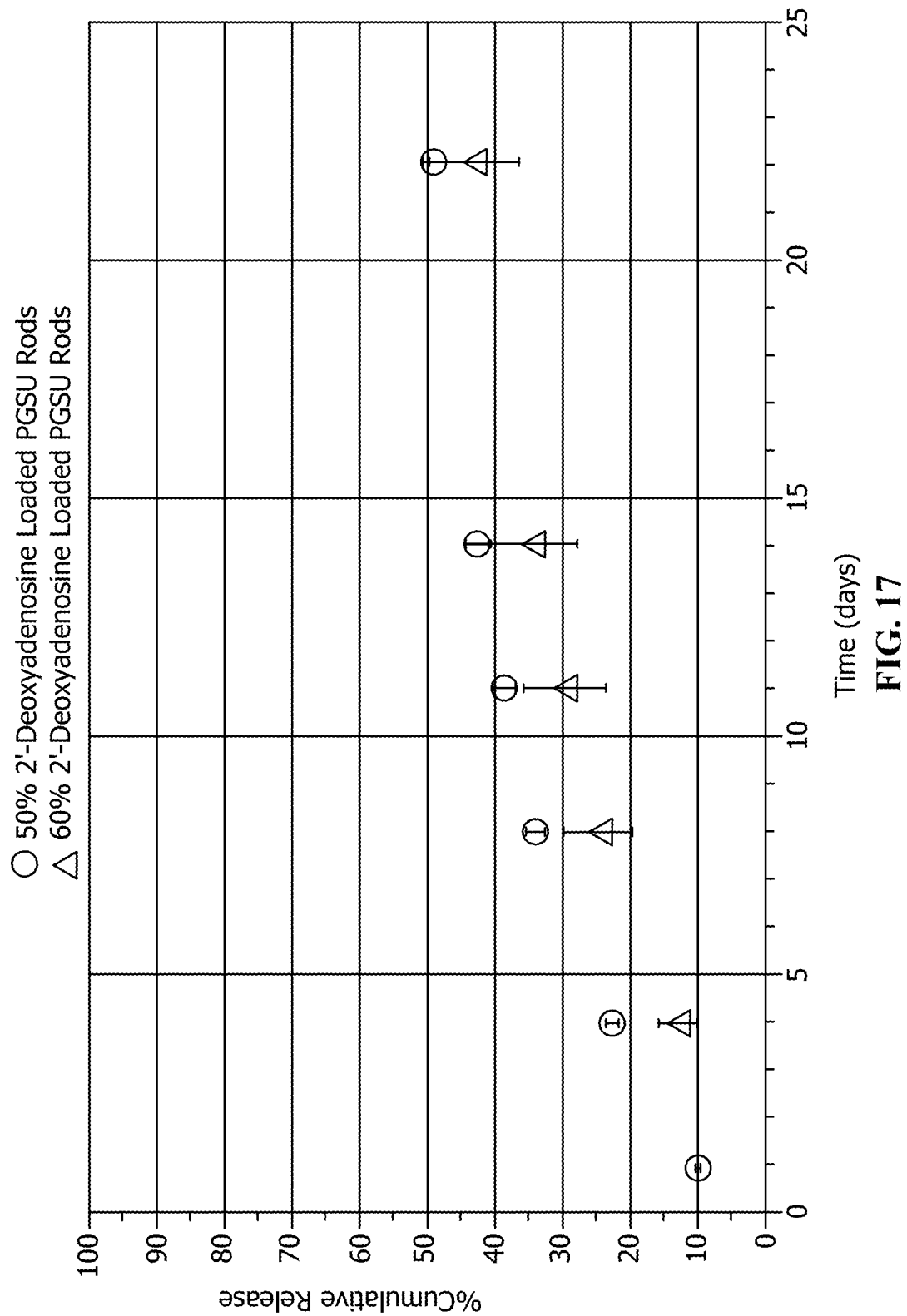
FIG. 17 graphically illustrates API release as a function of time for a controlled release device under acidic conditions in accordance with an aspect described herein.

Single-component PGSU rods having a 3-mm cross-sectional diameter were made in the manner described with respect to Example 1 but loaded with 2'-deoxyadenosine as a model drug. The rods were loaded with either 50% or 60% w/w drug using a solvent-free composition. Rods of both loadings were then placed in SGF at 37° C. Cumulative release was determined over time, as reflected in FIG. 17, and demonstrates crosslinked PGS such as PGSU can sustain release of highly soluble drugs in highly acidic gastric conditions without compromising the controlled release performance or mechanical integrity.

Figure 18:
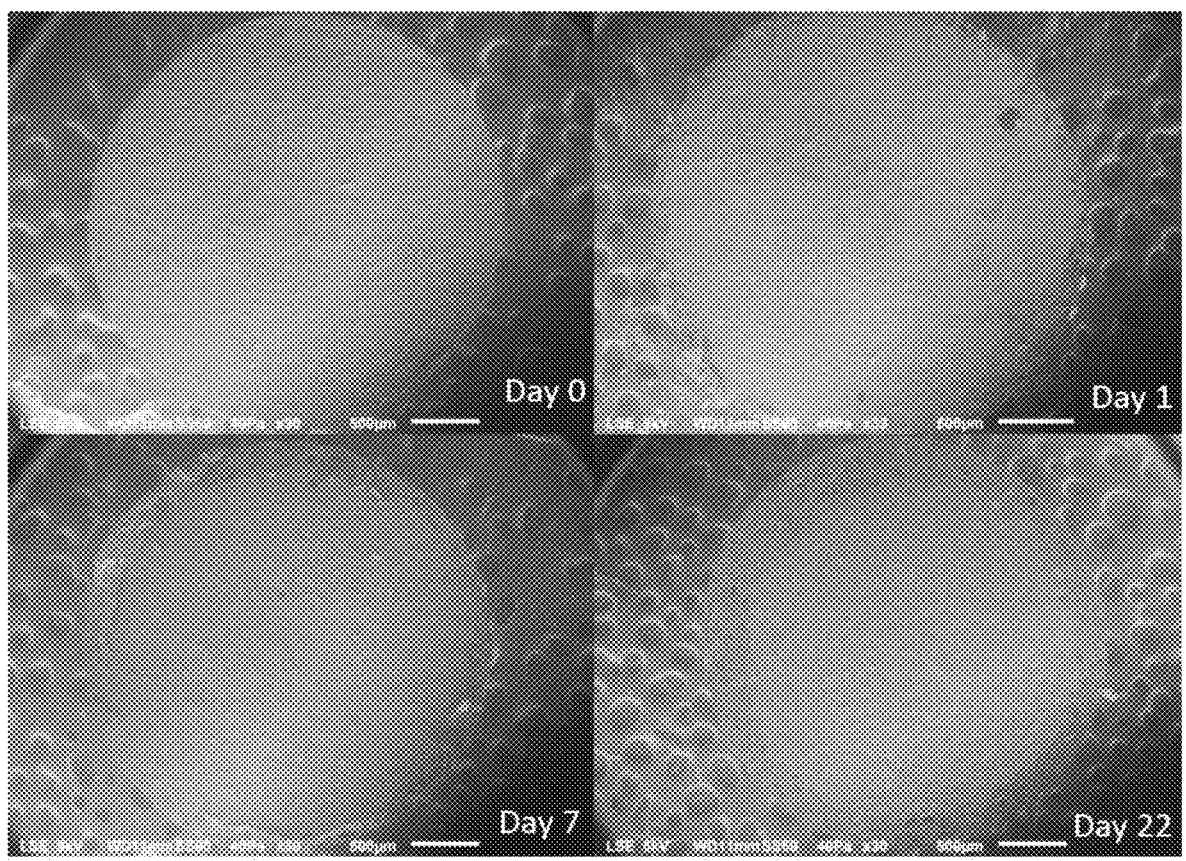
FIG. 18 illustrates degradation over time for a controlled release device under acidic conditions in accordance with an aspect described herein.

FIG. 18 shows SEM images of a rod at 50% w/w loading as a function of time, at zero, one, seven, and 22 days. A slight ring of diffusion of highly soluble drug can be observed around the periphery by the porosity left behind at the edge. The increased surface area on the periphery accelerates surface erosion. When the PGSU is formulated with very soluble drugs at high loadings, diffusion and erosion occur in concert, leading to diameter reduction and then finally complete degradation of the PGSU shortly after drug payload depletion.

Examples 13-18

Figure 19:
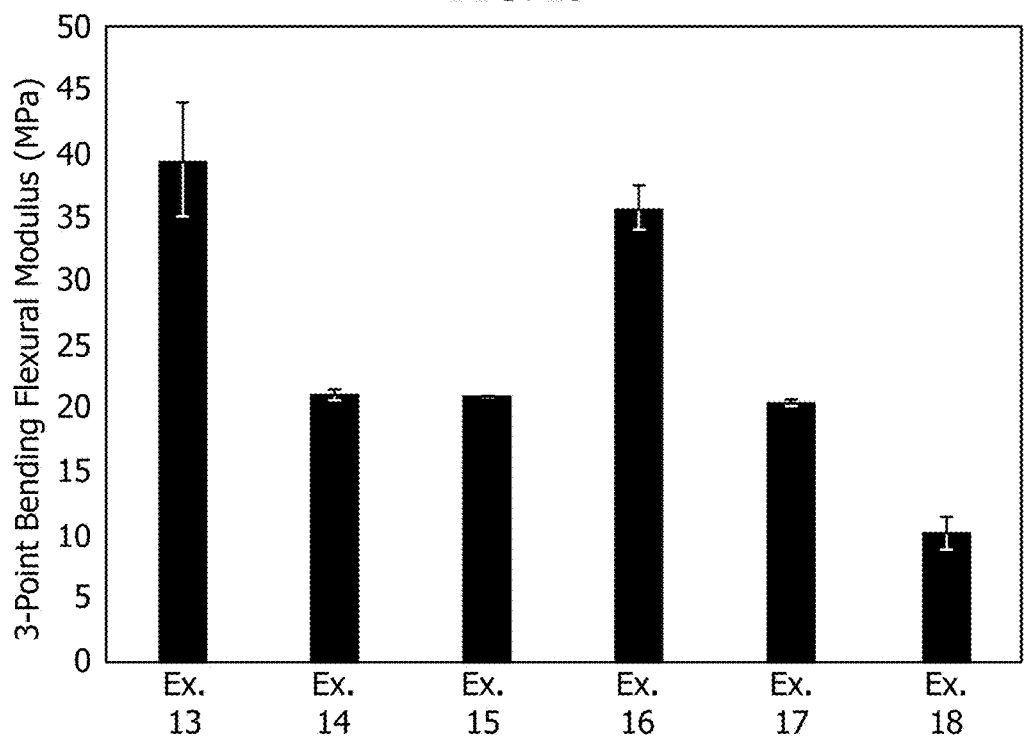
FIG. 19 graphically illustrates a 3-point bending flexural modulus of controlled release devices for six different conditions in accordance with an aspect described herein.

PGSU rods having a circular cross-sectional diameter of 3 mm were injection molded using both solvated and solvent free compositions at different crosslinking densities using HDI as the crosslinking agent and at different loadings of active ingredients. Flexural modulus of each was measured using a three point bending test, per ASTM D790. The composition of each is shown in Table 1, and the results are reflected in the graph shown at FIG. 19.

TABLE 1

PGSU Rod Compositions

| Example | Solvation State | PGS:HDI (w:w) | Active - Type/Amt |
|---|---|---|---|
| 13 | Solvent-free | 3.5:1 | 40% w/w 2'-deoxyadenosine |
| 14 | 60% PGS solution | 3.5:1 | 40% w/w 2'-deoxyadenosine |
| 15 | Solvent-free | 3.5:1 | 30% w/w 2'-deoxyadenosine |
| 16 | 60% PGS solution | 4:1 | 50% w/w 2'-deoxyadenosine |
| 17 | 60% PGS solution | 4.5:1 | 40% w/w caffeine |
| 18 | 60% PGS solution | 3.5:1 | 40% w/w phenazone |

Example 19

PGSU rings of a hydrodynamic radius of 17.5 mm (diameter of 35 mm) with a rectangular cross-section of 9 mm height and 2 mm thickness were injection molded using a solvent free composition with a 3.5:1 PGS:HDI w:w ratio and 50% w/w phenazone loading. The resulting drug-loaded PGSU ring was found to be sufficiently flexible to bend for insertion into a hard-shelled gelatin capsule in a contracted state.

Example 20

PGSU rings of a hydrodynamic radius of 22.5 mm (diameter of 45 mm) with a rectangular cross-section of 9 mm height and 1.2 mm thickness were injection molded using a solvated composition of 60% w/w PGS solution and HDI at a 3.5:1 PGS:HDI w:w ratio along with 40% w/w 2'-deoxyadenosine loading. The resulting loaded PGSU ring was found to be sufficiently flexible to bend for insertion into a hard-shelled gelatin capsule in a contracted state.

Other than in the examples, or where otherwise indicated, all numbers expressing quantities are to be understood as being modified in all instances by the term "about", meaning within 10% of the indicated number (e.g. "about 10%" means 9% to 11% and "about 2%" means 1.8% to 2.2%).

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints.

All above-mentioned references are hereby incorporated by reference herein.

While the invention has been described with reference to one or more exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention but that the invention will include all embodiments falling within the scope of the appended claims. In addition, all numerical values identified in the detailed description shall be interpreted as though the precise and approximate values are both expressly identified.

What is claimed is:

1. A delivery system comprising:
a controlled release device provided in a contracted state and expandable to a three-dimensional expanded state in a stomach for retention in the stomach based on the three-dimensional expanded state, wherein the controlled release device is a single composition comprising crosslinked poly(glycerol sebacate) (PGS) and a controlled release compound loaded in the crosslinked PGS, wherein the controlled release device does not comprise biodegradable linkers.

2. The delivery system of claim 1 further comprising a delivery vehicle maintaining the controlled release device in the contracted state prior to reaching the stomach.

3. The delivery system of claim 2, wherein the delivery vehicle is a capsule.

4. The delivery system of claim 1, wherein the controlled release compound comprises an active pharmaceutical ingredient.

5. The delivery system of claim 1, wherein the three-dimensional expanded state is configured to maintain the controlled release device at the stomach for a predetermined period of time until the crosslinked PGS of the controlled release device is biodegraded sufficiently for the controlled release device to leave the stomach.

6. The delivery system of claim 1, wherein the controlled release device in the three-dimensional expanded state is a ring.

7. The delivery system of claim 6, wherein the ring has a single complete break in its perimeter.

8. The delivery system of claim 6, wherein the ring has a non-circular geometry comprising at least one straight side.

9. The delivery system of claim 8, wherein the ring includes at least one region configured to aid facile bending, folding or both.

10. The delivery system of claim 1, wherein at least a portion of the controlled release device has a circular cross-section.

11. The delivery system of claim 1, wherein at least a portion of the controlled release device has a non-circular cross-section.

12. The delivery system of claim 1, wherein the controlled release device is free of polymer other than the crosslinked PGS.

13. The delivery system of claim 1, wherein the crosslinked PGS is poly(glycerol sebacate) urethane.

14. The delivery system of claim 1, wherein the controlled release compound has a predetermined particle size to provide the controlled release device with a predetermined controlled release profile.

15. The delivery system of claim 1, wherein the controlled release compound is present in the controlled release device in the range of 5% to 80% w/w of the crosslinked PGS.

16. A process of forming a delivery system, the process comprising:
   forming a controlled release device expandable to a three-dimensional expanded state in a stomach for retention in the stomach based on the three-dimensional expanded state, wherein the controlled release device is a single composition comprising crosslinked poly(glycerol sebacate) (PGS) and a controlled release compound loaded in the crosslinked PGS, wherein the controlled release device does not comprise biodegradable linkers; and
   confining the controlled release device in a delivery vehicle in a contracted state to form the delivery system.

17. The process of claim 16, wherein the crosslinked PGS is crosslinked by a system selected from the group consisting of urethane chemistry, thermosetting, acrylate chemistry, and photopolymerization chemistry.

18. The process of claim 16, wherein the forming is selected from the group consisting of extruding, additive manufacturing, molding, casting, and stamping.

19. The process of claim 16, wherein the forming further comprises loading the controlled release device with the controlled release compound.

20. The process of claim 16, wherein the forming further comprises injection molding a PGS resin, an isocyanate, and the controlled release compound to form the controlled release device.

21. The process of claim 20, wherein the injection molding creates the controlled release device as a single component.

22. The process of claim 20, wherein the injection molding orients polymer chains of the crosslinked PGS, controlled release compound, or both within the controlled release device.

23. The process of claim 16, wherein the crosslinked PGS is poly(glycerol sebacate) urethane.

24. The process of claim 16, wherein the controlled release compound comprises at least one active pharmaceutical ingredient.

25. A method of treatment comprising:
   orally administering a delivery system to a patient in need thereof;
   wherein the delivery system is provided in a contracted state and expands to a three-dimensional expanded state in a stomach of the patient for retention in the stomach based on the three-dimensional expanded state, wherein the controlled release device is a single composition comprising crosslinked poly(glycerol sebacate) (PGS) and a controlled release compound loaded in the crosslinked PGS, wherein the controlled release device does not comprise biodegradable linkers;
   wherein the controlled release device is retained in the stomach by the shape of the three-dimensional expanded state;
   wherein the delivery system provides direct gastric feeding to the patient; and
   wherein the patient is selected from the group consisting of a dysphagic patient, a premature infant, an unconscious patient, a surgically compromised patient, and a traumatically injured patient.

* * * * *